US008334427B2

United States Patent
Yin et al.

(10) Patent No.: US 8,334,427 B2
(45) Date of Patent: Dec. 18, 2012

(54) **INDUCTION OF XA27 BY THE AVRXA27 GENE IN RICE CONFERS BROAD-SPECTRUM RESISTANCE TO *XANTHOMONAS ORYZAE* PV. *ORYZAE* AND ENHANCED RESISTANCE TO *XANTHOMONAS ORYZAE* PV. *ORYZICOLA***

(75) Inventors: Zhongchao Yin, Singapore (SG); Dongsheng Tian, Singapore (SG)

(73) Assignee: Temasek Life Sciences Laboratory, Singapore (SG)

( * ) Notice: Subject to any disclaimer, the term of this patent is extended or adjusted under 35 U.S.C. 154(b) by 485 days.

(21) Appl. No.: 12/524,259

(22) PCT Filed: Jan. 8, 2008

(86) PCT No.: PCT/SG2008/000005
§ 371 (c)(1),
(2), (4) Date: Nov. 17, 2009

(87) PCT Pub. No.: WO2008/094127
PCT Pub. Date: Aug. 7, 2008

(65) Prior Publication Data
US 2010/0162438 A1     Jun. 24, 2010

Related U.S. Application Data

(60) Provisional application No. 60/897,864, filed on Jan. 29, 2007.

(51) Int. Cl.
*C12N 15/09* (2006.01)
*C12N 15/82* (2006.01)
*A01H 5/00* (2006.01)

(52) U.S. Cl. ...... 800/279; 800/278; 800/298; 800/320.2; 800/287; 800/314; 800/317.1; 800/317.4; 800/306; 800/313; 800/307; 800/301; 800/320.1; 435/69.1

(58) Field of Classification Search ........................ None
See application file for complete search history.

(56) References Cited

U.S. PATENT DOCUMENTS 6,586,657 B2 * 7/2003 Briggs et al. .................. 800/279

FOREIGN PATENT DOCUMENTS

| WO | 00/09698 A2 | 2/2000 |
| WO | 01/62896 A2 | 8/2001 |
| WO | 2005/017158 A1 | 2/2005 |

OTHER PUBLICATIONS

Gu, K. et al., "R gene expression induced by a type-III effector triggers disease resistance in rice," Nature, 2005, vol. 435(23), pp. 1122-1125.

* cited by examiner

*Primary Examiner* — Medina A Ibrahim
(74) *Attorney, Agent, or Firm* — Rothwell, Figg, Ernst & Manbeck P.C.

(57) ABSTRACT

The present invention generally provides a method to generate broad-spectrum resistance to bacterial blight disease in plants. More specifically, the present invention provides a method to generate broad-spectrum resistance to *Xanthomonas oryzae* pv. *oryzae*, the causal agent of bacterial blight disease of rice, and enhanced resistance to *Xanthomonas oryzae* pv. *oryzicola*, the causal agent of bacterial leaf streak of rice. Xa27, an inducible bacterial blight R gene in rice, was induced by the cognate avrXa27 gene expressed in host. Rice plants carrying the avrXa27 transgene and wild-type Xa27 gene conferred resistance to incompatible and compatible pathogens, and enhanced resistance to *X. oryzae* pv. *oryzicola* strain L8. The Xa27-mediated enhanced resistance to *X. oryzae* pv. *oryzicola* was also observed in the interaction between IRBB27 and L8 harboring pHM1avrXa27. This was further verified by the fact that the Xa27 gene in IRBB27 was induced by the avrXa27 gene in bacteria. The method can be used to engineer broad-spectrum resistance of rice to bacterial blight and enhanced resistance to bacterial leaf streak. Slight modification of this technique can be applied to control bacterial diseases in other crops.

35 Claims, 4 Drawing Sheets

SEQUENCE LISTING

```
<160> NUMBER OF SEQ ID NOS: 9

<210> SEQ ID NO 1
<211> LENGTH: 3411
<212> TYPE: DNA
<213> ORGANISM: Xanthomonas oryzae
<220> FEATURE:
<221> NAME/KEY: CDS
<222> LOCATION: (1)..(3411)

<400> SEQUENCE: 1 atg gat ccc att cgt tcg cgc acg cca agt cct gcc cgc gag ctt ctg      48
Met Asp Pro Ile Arg Ser Arg Thr Pro Ser Pro Ala Arg Glu Leu Leu
1               5                   10                  15 ccc gga ccc caa ccg gat agg gtt cag ccg act gca gat cgg ggg ggg      96
Pro Gly Pro Gln Pro Asp Arg Val Gln Pro Thr Ala Asp Arg Gly Gly
            20                  25                  30 gct ccg cct gct ggc ggc ccc ctg gat ggc ttg ccc gct cgg cgg acg     144
Ala Pro Pro Ala Gly Gly Pro Leu Asp Gly Leu Pro Ala Arg Arg Thr
        35                  40                  45 atg tcc cgg acc cgg ctg cca tct ccc cct gcg ccc tcg cct gcg ttc     192
Met Ser Arg Thr Arg Leu Pro Ser Pro Pro Ala Pro Ser Pro Ala Phe
    50                  55                  60 tcg gcg ggc agc ttc aac gat ctg ctc cgt cag ttc gat ccg tcg ctt     240
Ser Ala Gly Ser Phe Asn Asp Leu Leu Arg Gln Phe Asp Pro Ser Leu
65                  70                  75                  80 ctt gat aca tcg ctt ctt gat tcg atg cct gcc gtc ggc acg ccg cat     288
Leu Asp Thr Ser Leu Leu Asp Ser Met Pro Ala Val Gly Thr Pro His
                85                  90                  95 aca gcg gct gcc cca gca gag tgg gat gag gtg caa tcg ggt ctg cgt     336
Thr Ala Ala Ala Pro Ala Glu Trp Asp Glu Val Gln Ser Gly Leu Arg
```

```
                    100                 105                 110
gca gcc gat gac ccg cca ccc acc gtg cgt gtc gct gtc act gcc gcg          384
Ala Ala Asp Asp Pro Pro Pro Thr Val Arg Val Ala Val Thr Ala Ala
            115                 120                 125 cgg ccg ccg cgc gcc aag ccg gcc ccg cga cgg cgt gcg gca ccc              432
Arg Pro Pro Arg Ala Lys Pro Ala Pro Arg Arg Ala Ala Gln Pro
130                 135                 140 tcc gac gct tcg ccg gcc gcg cag gtg gat cta cgc acg ctc ggc tac          480
Ser Asp Ala Ser Pro Ala Ala Gln Val Asp Leu Arg Thr Leu Gly Tyr
145                 150                 155                 160 agt cag cag cag caa gag aag atc aaa tcg aag gtg cgt tcg aca gtg          528
Ser Gln Gln Gln Gln Glu Lys Ile Lys Ser Lys Val Arg Ser Thr Val
                165                 170                 175 gcg cag cac cac gag gca ctg gtg ggc cat ggg ttt aca cac gcg cac          576
Ala Gln His His Glu Ala Leu Val Gly His Gly Phe Thr His Ala His
            180                 185                 190 atc gtt gcg ctc agc caa cac ccg gca gcg tta ggg acc gtc gct gtc          624
Ile Val Ala Leu Ser Gln His Pro Ala Ala Leu Gly Thr Val Ala Val
            195                 200                 205 aag tat cag cac ata atc acg gcg ttg cca gag gcg aca cac gaa gac          672
Lys Tyr Gln His Ile Ile Thr Ala Leu Pro Glu Ala Thr His Glu Asp
210                 215                 220 atc gtt ggc gtc ggc aaa cag tgg tcc ggc gca cgc gcc ctg gag gcc          720
Ile Val Gly Val Gly Lys Gln Trp Ser Gly Ala Arg Ala Leu Glu Ala
225                 230                 235                 240 ttg ctc acg aag gcg ggg gag ttg aga ggt ccg ccg tta cag ttg gac          768
Leu Leu Thr Lys Ala Gly Glu Leu Arg Gly Pro Pro Leu Gln Leu Asp
                245                 250                 255 aca ggc caa ctt ctc aag att gca aaa cgt ggc ggc gtg acc gca gtg          816
Thr Gly Gln Leu Leu Lys Ile Ala Lys Arg Gly Gly Val Thr Ala Val
            260                 265                 270 gag gca gtg cat gca tcg cgc aat gca ctg acg ggt gcc ccc ctg aac          864
Glu Ala Val His Ala Ser Arg Asn Ala Leu Thr Gly Ala Pro Leu Asn
            275                 280                 285 ctg acc ccg gac caa gtg gtg gcc atc gcc agc aat att ggc ggc aac          912
Leu Thr Pro Asp Gln Val Val Ala Ile Ala Ser Asn Ile Gly Gly Asn
290                 295                 300 cag gcg ctg gag acg gtg cag cgg ctg ttg ccg gtg ctg tgc cag gac          960
Gln Ala Leu Glu Thr Val Gln Arg Leu Leu Pro Val Leu Cys Gln Asp
305                 310                 315                 320 cat ggc ctg acc ccg gac caa gtg gtg gcc atc gcc aac aat aac ggc         1008
His Gly Leu Thr Pro Asp Gln Val Val Ala Ile Ala Asn Asn Asn Gly
                325                 330                 335 ggc aag cag gcg ctg gag acg gtg cag cgg ctg ttg ccg gtg ctg tgc         1056
Gly Lys Gln Ala Leu Glu Thr Val Gln Arg Leu Leu Pro Val Leu Cys
            340                 345                 350 cag gcc cat ggc ctg acc ccg gac caa gtg gtg gcc atc gcc agc aat         1104
Gln Ala His Gly Leu Thr Pro Asp Gln Val Val Ala Ile Ala Ser Asn
            355                 360                 365 ggc ggc aag cag gcg ctg gag acg gtg cag cgg ctg ttg ccg gtg ctg         1152
Gly Gly Lys Gln Ala Leu Glu Thr Val Gln Arg Leu Leu Pro Val Leu
370                 375                 380 tgc cag gcc cat ggc ctg acc ccg aac cag gtc gtg gcc atc gcc agc         1200
Cys Gln Ala His Gly Leu Thr Pro Asn Gln Val Val Ala Ile Ala Ser
385                 390                 395                 400 aat ggc ggc ggc aag cag gcg ctg gag acg gtg cag cgg ctg ttg ccg         1248
Asn Gly Gly Gly Lys Gln Ala Leu Glu Thr Val Gln Arg Leu Leu Pro
                405                 410                 415 gtg ctg tgc cag gcc cat ggc ctg acc cag gac cag gtg gtg gcc atc         1296
Val Leu Cys Gln Ala His Gly Leu Thr Gln Asp Gln Val Val Ala Ile
```

-continued

```
              420                 425                 430
gcc agc aat agt ggc ggc aag cag gcg ctg gag acg gtg cag cgg ctg    1344
Ala Ser Asn Ser Gly Gly Lys Gln Ala Leu Glu Thr Val Gln Arg Leu
        435                 440                 445 ttg ccg gtg ctg tgc cag gcc cat ggc ctg acc ccg gcc caa gtg gtg    1392
Leu Pro Val Leu Cys Gln Ala His Gly Leu Thr Pro Ala Gln Val Val
450                 455                 460 gcc atc gcc agc aat aac ggc ggc aag cag gcg ctg gag acg gtg cag    1440
Ala Ile Ala Ser Asn Asn Gly Gly Lys Gln Ala Leu Glu Thr Val Gln
465                 470                 475                 480 cgg ctg ttt ccg gtg ctg tgc cag gac cat ggc ctg acc ccg gac cag    1488
Arg Leu Phe Pro Val Leu Cys Gln Asp His Gly Leu Thr Pro Asp Gln
                485                 490                 495 gtg gtg acc atc gcc aac aat aac ggc ggc aag cag gcg ctg gag acg    1536
Val Val Thr Ile Ala Asn Asn Asn Gly Gly Lys Gln Ala Leu Glu Thr
        500                 505                 510 gtg cag cgg ctg ttg ccg gtg ctg tgc cag gcc cat ggc ttg atc ccg    1584
Val Gln Arg Leu Leu Pro Val Leu Cys Gln Ala His Gly Leu Ile Pro
            515                 520                 525 gac cag gtg gtg gcc atc gcc aac aat aac ggc ggc aag cag gcg ctg    1632
Asp Gln Val Val Ala Ile Ala Asn Asn Asn Gly Gly Lys Gln Ala Leu
530                 535                 540 gag acg gtg cag cgg ctg ttg ccg gtg ctg tgc cag gcc cat ggc ctg    1680
Glu Thr Val Gln Arg Leu Leu Pro Val Leu Cys Gln Ala His Gly Leu
545                 550                 555                 560 acc ccg gcc caa gtg gtg gcc atc gcc agc aat att ggc ggc aag cag    1728
Thr Pro Ala Gln Val Val Ala Ile Ala Ser Asn Ile Gly Gly Lys Gln
                565                 570                 575 gcg ctg gag acg gtg cag cgg ctg ttg ccg gtg ctg tgc cgg gcc cat    1776
Ala Leu Glu Thr Val Gln Arg Leu Leu Pro Val Leu Cys Arg Ala His
            580                 585                 590 ggc ctg acc ccg gcc caa gtg gtg gcc atc gcc aac aat aac ggc ggc    1824
Gly Leu Thr Pro Ala Gln Val Val Ala Ile Ala Asn Asn Asn Gly Gly
        595                 600                 605 aag cag gcg ctg gag acg gtg cag cgg ctg ttg ccg gtg ctg tgc cag    1872
Lys Gln Ala Leu Glu Thr Val Gln Arg Leu Leu Pro Val Leu Cys Gln
610                 615                 620 gcc cat ggc ctg acc ccg gat caa gtg gtg gcc atc gcc agc aat att    1920
Ala His Gly Leu Thr Pro Asp Gln Val Val Ala Ile Ala Ser Asn Ile
625                 630                 635                 640 ggc ggc aag cag gcg ctg gag acg gtg cag cgc ctg ttg ccg gtg ctg    1968
Gly Gly Lys Gln Ala Leu Glu Thr Val Gln Arg Leu Leu Pro Val Leu
                645                 650                 655 tgc cag gac cat ggc ctg acc ccg gac cag gtc gtg gcc atc gcc agc    2016
Cys Gln Asp His Gly Leu Thr Pro Asp Gln Val Val Ala Ile Ala Ser
            660                 665                 670 aat ggc ggc aag cag gcg ctg gag acg gtg cag cgg ctg ttg ccg gtg    2064
Asn Gly Gly Lys Gln Ala Leu Glu Thr Val Gln Arg Leu Leu Pro Val
        675                 680                 685 ctg tgc cag gac cat ggc ctg acc ccg gcc cag gtg gtg gcc atc gcc    2112
Leu Cys Gln Asp His Gly Leu Thr Pro Ala Gln Val Val Ala Ile Ala
690                 695                 700 agc cac gat ggc ggc aag cag gcg ctg gag acg gtg cag cgg ctg ttg    2160
Ser His Asp Gly Gly Lys Gln Ala Leu Glu Thr Val Gln Arg Leu Leu
705                 710                 715                 720 ccg gtg ctg tgc cag gac cat ggc ctg acc ctg gac cag gtc gtg gcc    2208
Pro Val Leu Cys Gln Asp His Gly Leu Thr Leu Asp Gln Val Val Ala
                725                 730                 735 atc gcc agc cac gat ggc ggc aag cag gcg ctg gag acg gtg cag cgg    2256
Ile Ala Ser His Asp Gly Gly Lys Gln Ala Leu Glu Thr Val Gln Arg
```

```
                    740                 745                 750
ctg ttg ccg gtg ctg tgc cag gac cat ggc ctg acc ctg gac cag gtg        2304
Leu Leu Pro Val Leu Cys Gln Asp His Gly Leu Thr Leu Asp Gln Val
        755                 760                 765 gtg gcc atc gcc agc aat att ggc ggc aag cag gcg ctg gag acg gtg        2352
Val Ala Ile Ala Ser Asn Ile Gly Gly Lys Gln Ala Leu Glu Thr Val
770                 775                 780 cag cgg ctg ttg ccg gtg ctg tgc cag gac cat ggc ctg acc ccg gac        2400
Gln Arg Leu Leu Pro Val Leu Cys Gln Asp His Gly Leu Thr Pro Asp
785                 790                 795                 800 cag gtc gtg gcc atc gcc agc aat ggc ggc ggc aag cag gcg ctg gag        2448
Gln Val Val Ala Ile Ala Ser Asn Gly Gly Gly Lys Gln Ala Leu Glu
            805                 810                 815 acg gtg caa cgg ctg ttg ccg gtg ctg tgc cag gac cat ggc ctg acc        2496
Thr Val Gln Arg Leu Leu Pro Val Leu Cys Gln Asp His Gly Leu Thr
        820                 825                 830 ccg gac cag gtc gtg gcc atc gcc agc aat ggc ggc ggc aag cag gcg        2544
Pro Asp Gln Val Val Ala Ile Ala Ser Asn Gly Gly Gly Lys Gln Ala
            835                 840                 845 ctg gag agc att gtt gcc cag tta tct cgc cct gat ccg gcg ttg gcc        2592
Leu Glu Ser Ile Val Ala Gln Leu Ser Arg Pro Asp Pro Ala Leu Ala
850                 855                 860 gcg ttg acc aac gac cac ctc gtc gcc ttg gcc tgc ctc ggc gga cgt        2640
Ala Leu Thr Asn Asp His Leu Val Ala Leu Ala Cys Leu Gly Gly Arg
865                 870                 875                 880 cct gcc ctg gat gca gtg aaa aag gga ttg ccg cac gcg ccg gaa ttg        2688
Pro Ala Leu Asp Ala Val Lys Lys Gly Leu Pro His Ala Pro Glu Leu
                885                 890                 895 atc aga aga atc aat cgc cgt att ccc gaa cgc acg tcc cat cgc gtt        2736
Ile Arg Arg Ile Asn Arg Arg Ile Pro Glu Arg Thr Ser His Arg Val
            900                 905                 910 gcc gac ctc gcg cac gtg gtg cgc gtg ctt ggt ttt ttc cag agc cac        2784
Ala Asp Leu Ala His Val Val Arg Val Leu Gly Phe Phe Gln Ser His
        915                 920                 925 tcc cac cca gcg caa gca ttc gat gac gcc atg acg cag ttc ggg atg        2832
Ser His Pro Ala Gln Ala Phe Asp Asp Ala Met Thr Gln Phe Gly Met
930                 935                 940 agc agg cac ggg ttg gta cag ctc ttt cgc aga gtg ggc gtc acc gaa        2880
Ser Arg His Gly Leu Val Gln Leu Phe Arg Arg Val Gly Val Thr Glu
945                 950                 955                 960 ttc gaa gcc cgc tgc gga acg ctc ccc cca gcc tcg cag cgt tgg gac        2928
Phe Glu Ala Arg Cys Gly Thr Leu Pro Pro Ala Ser Gln Arg Trp Asp
                965                 970                 975 cgt atc ctc cag gca tca ggg atg aaa agg gcc aaa ccg tcc cct act        2976
Arg Ile Leu Gln Ala Ser Gly Met Lys Arg Ala Lys Pro Ser Pro Thr
            980                 985                 990 tca gct caa acg ccg gat cag gcg tct ttg cat gca ttc gcc gat tcg        3024
Ser Ala Gln Thr Pro Asp Gln Ala Ser Leu His Ala Phe Ala Asp Ser
        995                 1000                1005 ctg gag cgt gac ctt gat gcg ccc agc cca atg cac gag gga gat        3069
Leu Glu Arg Asp Leu Asp Ala Pro Ser Pro Met His Glu Gly Asp
    1010                1015                1020 cag acg cgg gca agc agc cgt aaa cgg tcc cga tcg gat cgt gct        3114
Gln Thr Arg Ala Ser Ser Arg Lys Arg Ser Arg Ser Asp Arg Ala
    1025                1030                1035 gtc acc ggc ccc tcc aca cag caa tct ttc gag gtg cgc gtt ccc        3159
Val Thr Gly Pro Ser Thr Gln Gln Ser Phe Glu Val Arg Val Pro
    1040                1045                1050 gaa cag cgc gat gcg ctg cat ttg ccc ctc agc tgg agg gta aaa        3204
Glu Gln Arg Asp Ala Leu His Leu Pro Leu Ser Trp Arg Val Lys
```

-continued

```
                            1055                1060                1065
cgc ccg cgt acc agg atc ggg ggc ggc ctc ccg gat cct ggt acg        3249
Arg Pro Arg Thr Arg Ile Gly Gly Gly Leu Pro Asp Pro Gly Thr
        1070                1075                1080 ccc atc gct gcc gac ctg gca gcg tcc agc acc gtg atg tgg gaa        3294
Pro Ile Ala Ala Asp Leu Ala Ala Ser Ser Thr Val Met Trp Glu
        1085                1090                1095 caa gat gcg gcc ccc ttc gca ggg gca gcg gat gat ttc ccg gca        3339
Gln Asp Ala Ala Pro Phe Ala Gly Ala Ala Asp Asp Phe Pro Ala
        1100                1105                1110 ttc aac gaa gag gag ctc gca tgg ttg atg gag cta ttg cct cag        3384
Phe Asn Glu Glu Glu Leu Ala Trp Leu Met Glu Leu Leu Pro Gln
        1115                1120                1125 tca ggc tca gtc gga ggg acg atc tga                                3411
Ser Gly Ser Val Gly Gly Thr Ile
        1130                1135

<210> SEQ ID NO 2
<211> LENGTH: 1136
<212> TYPE: PRT
<213> ORGANISM: Xanthomonas oryzae

<400> SEQUENCE: 2

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly
                20                  25                  30

Ala Pro Pro Ala Gly Gly Pro Leu Asp Gly Leu Pro Ala Arg Arg Thr
            35                  40                  45

Met Ser Arg Thr Arg Leu Pro Ser Pro Ala Pro Ser Pro Ala Phe
50                  55                  60

Ser Ala Gly Ser Phe Asn Asp Leu Leu Arg Gln Phe Asp Pro Ser Leu
65                  70                  75                  80

Leu Asp Thr Ser Leu Leu Asp Ser Met Pro Ala Val Gly Thr Pro His
                85                  90                  95

Thr Ala Ala Ala Pro Ala Glu Trp Asp Glu Val Gln Ser Gly Leu Arg
            100                 105                 110

Ala Ala Asp Asp Pro Pro Pro Thr Val Arg Val Ala Val Thr Ala Ala
        115                 120                 125

Arg Pro Pro Arg Ala Lys Pro Ala Pro Arg Arg Ala Ala Gln Pro
        130                 135                 140

Ser Asp Ala Ser Pro Ala Gln Val Asp Leu Arg Thr Leu Gly Tyr
145                 150                 155                 160

Ser Gln Gln Gln Gln Glu Lys Ile Lys Ser Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln His Ile Ile Thr Ala Leu Pro Glu Ala Thr His Glu Asp
        210                 215                 220

Ile Val Gly Val Gly Lys Gln Trp Ser Gly Ala Arg Ala Leu Glu Ala
225                 230                 235                 240

Leu Leu Thr Lys Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270
```

```
Glu Ala Val His Ala Ser Arg Asn Ala Leu Thr Gly Ala Pro Leu Asn
        275                 280                 285

Leu Thr Pro Asp Gln Val Val Ala Ile Ala Ser Asn Ile Gly Gly Asn
    290                 295                 300

Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Asn Asn Asn Gly
                325                 330                 335

Gly Lys Gln Ala Leu Glu Thr Val Gln Arg Leu Leu Pro Val Leu Cys
            340                 345                 350

Gln Ala His Gly Leu Thr Pro Asp Gln Val Val Ala Ile Ala Ser Asn
        355                 360                 365

Gly Gly Lys Gln Ala Leu Glu Thr Val Gln Arg Leu Leu Pro Val Leu
    370                 375                 380

Cys Gln Ala His Gly Leu Thr Pro Asn Gln Val Val Ala Ile Ala Ser
385                 390                 395                 400

Asn Gly Gly Lys Gln Ala Leu Glu Thr Val Gln Arg Leu Leu Pro
                405                 410                 415

Val Leu Cys Gln Ala His Gly Leu Thr Gln Asp Gln Val Val Ala Ile
        420                 425                 430

Ala Ser Asn Ser Gly Gly Lys Gln Ala Leu Glu Thr Val Gln Arg Leu
        435                 440                 445

Leu Pro Val Leu Cys Gln Ala His Gly Leu Thr Pro Ala Gln Val Val
    450                 455                 460

Ala Ile Ala Ser Asn Asn Gly Gly Lys Gln Ala Leu Glu Thr Val Gln
465                 470                 475                 480

Arg Leu Phe Pro Val Leu Cys Gln Asp His Gly Leu Thr Pro Asp Gln
                485                 490                 495

Val Val Thr Ile Ala Asn Asn Gly Gly Lys Gln Ala Leu Glu Thr
                500                 505                 510

Val Gln Arg Leu Leu Pro Val Leu Cys Gln Ala His Gly Leu Ile Pro
    515                 520                 525

Asp Gln Val Val Ala Ile Ala Asn Asn Gly Gly Lys Gln Ala Leu
    530                 535                 540

Glu Thr Val Gln Arg Leu Leu Pro Val Leu Cys Gln Ala His Gly Leu
545                 550                 555                 560

Thr Pro Ala Gln Val Val Ala Ile Ala Ser Asn Ile Gly Gly Lys Gln
                565                 570                 575

Ala Leu Glu Thr Val Gln Arg Leu Leu Pro Val Leu Cys Arg Ala His
        580                 585                 590

Gly Leu Thr Pro Ala Gln Val Val Ala Ile Ala Asn Asn Gly Gly
    595                 600                 605

Lys Gln Ala Leu Glu Thr Val Gln Arg Leu Leu Pro Val Leu Cys Gln
610                 615                 620

Ala His Gly Leu Thr Pro Asp Gln Val Val Ala Ile Ala Ser Asn Ile
625                 630                 635                 640

Gly Gly Lys Gln Ala Leu Glu Thr Val Gln Arg Leu Leu Pro Val Leu
            645                 650                 655

Cys Gln Asp His Gly Leu Thr Pro Asp Gln Val Val Ala Ile Ala Ser
                660                 665                 670

Asn Gly Gly Lys Gln Ala Leu Glu Thr Val Gln Arg Leu Leu Pro Val
                675                 680                 685

Leu Cys Gln Asp His Gly Leu Thr Pro Ala Gln Val Val Ala Ile Ala
```

```
                  690             695             700
Ser His Asp Gly Gly Lys Gln Ala Leu Glu Thr Val Gln Arg Leu Leu
705                     710                     715             720

Pro Val Leu Cys Gln Asp His Gly Leu Thr Leu Asp Gln Val Val Ala
                725                     730                 735

Ile Ala Ser His Asp Gly Gly Lys Gln Ala Leu Glu Thr Val Gln Arg
                    740                     745                 750

Leu Leu Pro Val Leu Cys Gln Asp His Gly Leu Thr Leu Asp Gln Val
                755                     760                 765

Val Ala Ile Ala Ser Asn Ile Gly Gly Lys Gln Ala Leu Glu Thr Val
                770                 775                 780

Gln Arg Leu Leu Pro Val Leu Cys Gln Asp His Gly Leu Thr Pro Asp
785                     790                     795             800

Gln Val Val Ala Ile Ala Ser Asn Gly Gly Lys Gln Ala Leu Glu
                    805                     810                 815

Thr Val Gln Arg Leu Leu Pro Val Leu Cys Gln Asp His Gly Leu Thr
                820                     825                 830

Pro Asp Gln Val Val Ala Ile Ala Ser Asn Gly Gly Lys Gln Ala
                835                     840                 845

Leu Glu Ser Ile Val Ala Gln Leu Ser Arg Pro Asp Pro Ala Leu Ala
850                     855                     860

Ala Leu Thr Asn Asp His Leu Val Ala Leu Ala Cys Leu Gly Gly Arg
865                     870                     875             880

Pro Ala Leu Asp Ala Val Lys Lys Gly Leu Pro His Ala Pro Glu Leu
                    885                     890                 895

Ile Arg Arg Ile Asn Arg Arg Ile Pro Glu Arg Thr Ser His Arg Val
                900                     905                 910

Ala Asp Leu Ala His Val Val Arg Val Leu Gly Phe Phe Gln Ser His
            915                     920                 925

Ser His Pro Ala Gln Ala Phe Asp Asp Ala Met Thr Gln Phe Gly Met
930                     935                     940

Ser Arg His Gly Leu Val Gln Leu Phe Arg Arg Val Gly Val Thr Glu
945                     950                     955             960

Phe Glu Ala Arg Cys Gly Thr Leu Pro Pro Ala Ser Gln Arg Trp Asp
                    965                     970                 975

Arg Ile Leu Gln Ala Ser Gly Met Lys Arg Ala Lys Pro Ser Pro Thr
                980                     985                 990

Ser Ala Gln Thr Pro Asp Gln Ala  Ser Leu His Ala Phe  Ala Asp Ser
                995                     1000                1005

Leu Glu  Arg Asp Leu Asp Ala  Pro Ser Pro Met His  Glu Gly Asp
        1010                    1015                1020

Gln Thr  Arg Ala Ser Ser Arg  Lys Arg Ser Arg Ser  Asp Arg Ala
        1025                    1030                1035

Val Thr  Gly Pro Ser Thr Gln  Gln Ser Phe Glu Val  Arg Val Pro
        1040                    1045                1050

Glu Gln  Arg Asp Ala Leu His  Leu Pro Leu Ser Trp  Arg Val Lys
        1055                    1060                1065

Arg Pro  Arg Thr Arg Ile Gly  Gly Gly Leu Pro Asp  Pro Gly Thr
        1070                    1075                1080

Pro Ile  Ala Ala Asp Leu Ala  Ala Ser Ser Thr Val  Met Trp Glu
        1085                    1090                1095

Gln Asp  Ala Ala Pro Phe Ala  Gly Ala Ala Asp Asp  Phe Pro Ala
        1100                    1105                1110
```

```
Phe Asn Glu Glu Glu Leu Ala Trp Leu Met Glu Leu Leu Pro Gln
    1115            1120                1125

Ser Gly Ser Val Gly Gly Thr Ile
    1130                1135

<210> SEQ ID NO 3
<211> LENGTH: 342
<212> TYPE: DNA
<213> ORGANISM: Oryza sativa
<220> FEATURE:
<221> NAME/KEY: CDS
<222> LOCATION: (1)..(342)

<400> SEQUENCE: 3 atg gcg gat tgg gcg atg cac cac tac ctc cta cta gcc aac cag caa      48
Met Ala Asp Trp Ala Met His His Tyr Leu Leu Leu Ala Asn Gln Gln
1               5                  10                  15 cgc cac cga gcc ctc gcc gac gtc gcc gtc cgc cgc cgc cag ctg ctc      96
Arg His Arg Ala Leu Ala Asp Val Ala Val Arg Arg Arg Gln Leu Leu
            20                  25                  30 ctc gac tcc ggc cgc gtc ttc atg ctc ctc ggc gcc gtc atc ctc atg     144
Leu Asp Ser Gly Arg Val Phe Met Leu Leu Gly Ala Val Ile Leu Met
        35                  40                  45 cac atg ctc acc act acc ggc ggc gga gca tcg tcc ggc tgc acc cgc     192
His Met Leu Thr Thr Thr Gly Gly Gly Ala Ser Ser Gly Cys Thr Arg
    50                  55                  60 ggc gcc gaa cct tgc gtc gcc ctc ctc ctg tgg ctg ctc ggc gcg gcg     240
Gly Ala Glu Pro Cys Val Ala Leu Leu Leu Trp Leu Leu Gly Ala Ala
65                  70                  75                  80 ctc gcc atg ctg tcg ctc gtc gcc ggc cga ttc ccc gtt ctc gct gcc     288
Leu Ala Met Leu Ser Leu Val Ala Gly Arg Phe Pro Val Leu Ala Ala
                85                  90                  95 gcc att gct gag gag ctc ggt gat cac ctg ctt ggt ggt ctc tgg tct     336
Ala Ile Ala Glu Glu Leu Gly Asp His Leu Leu Gly Gly Leu Trp Ser
            100                 105                 110 ctc tag                                                              342
Leu

<210> SEQ ID NO 4
<211> LENGTH: 113
<212> TYPE: PRT
<213> ORGANISM: Oryza sativa

<400> SEQUENCE: 4

Met Ala Asp Trp Ala Met His His Tyr Leu Leu Leu Ala Asn Gln Gln
1               5                  10                  15

Arg His Arg Ala Leu Ala Asp Val Ala Val Arg Arg Arg Gln Leu Leu
            20                  25                  30

Leu Asp Ser Gly Arg Val Phe Met Leu Leu Gly Ala Val Ile Leu Met
        35                  40                  45

His Met Leu Thr Thr Thr Gly Gly Gly Ala Ser Ser Gly Cys Thr Arg
    50                  55                  60

Gly Ala Glu Pro Cys Val Ala Leu Leu Leu Trp Leu Leu Gly Ala Ala
65                  70                  75                  80

Leu Ala Met Leu Ser Leu Val Ala Gly Arg Phe Pro Val Leu Ala Ala
                85                  90                  95

Ala Ile Ala Glu Glu Leu Gly Asp His Leu Leu Gly Gly Leu Trp Ser
            100                 105                 110

Leu
```

```
<210> SEQ ID NO 5
<211> LENGTH: 964
<212> TYPE: DNA
<213> ORGANISM: Oryza sativa

<400> SEQUENCE: 5
gaatttcttg gattccttta atttattcga gcgccacatg acggcttgag agtgtttata      60
ggaagtttaa tggacgtttt tgtatataat agatagatag atagatagat atcctccgtc     120
ccacaatata gggatttta gtttttgctt gcaatgtttg accactcgtc ttattcaaat      180
tttttttaca aatataaaaa atgaaaagtt gtgcttaaag tactgtagat aataaagtaa     240
gtcacaaata aataaataa taatttcaaa attttttgaa taagacaagt ggtcaaacgt      300
tgaaagcaaa aactcaaaat cccttatatt atgggacaga gggactagaa gatagttttt     360
gtatgtgttg ttcgatgttt tacgctccca aatatattaa tactacattg gatcaccatt     420
ttaaatttat tatagataag tttaatacga aaatttcaga tttgttttct taattttttat    480 gaacaacatt tgcatacaac atctggtcgt aataactacg ttgaatatta ccctcttgat     540
gacttgacta attttagaca aaagatggtc acccacccag ctttcattg aaagtataag      600 agttcgtaca gtgcaaaaag gaacaaaggt aaaataaaag gaaagtaaaa atcccaagtc     660
ctgcgtacaa atctatagtt caagacatac acatcgcctt ccaactgagg tcgagttgcc     720
ccggtgccat gtcttattcg tggaattcta tgtccaagtg catactttgc gggggtaaaa    780
ttttctacac gtatgttgcc aaaatttctg ctaagtttc gtgccaactc gagaaattct      840
tacacagcct gcagtctata aatattcaca catttcacaa aaaatactt gcaacatcaa      900 agctacacag gtagaatcat cgaccgtaag taggtacgta cattaagtgt gagcttgatt     960
aact                                                                  964

<210> SEQ ID NO 6
<211> LENGTH: 24
<212> TYPE: DNA
<213> ORGANISM: Oryza sativa

<400> SEQUENCE: 6
ccatgattac gaattcgagc tcgg                                             24

<210> SEQ ID NO 7
<211> LENGTH: 23
<212> TYPE: DNA
<213> ORGANISM: Oryza sativa

<400> SEQUENCE: 7
aagaagcgac ggatcgaact gac                                              23

<210> SEQ ID NO 8
<211> LENGTH: 24
<212> TYPE: DNA
<213> ORGANISM: Agrobacterium tumefaciens

<400> SEQUENCE: 8
cgaagaggag ctcgcatggt tgat                                             24

<210> SEQ ID NO 9
<211> LENGTH: 26
```

```
<212> TYPE: DNA
<213> ORGANISM: Agrobacterium tumefaciens

<400> SEQUENCE: 9
cactgatagt ttaattcccg atctag                                              26
```

INDUCTION OF XA27 BY THE AVRXA27 GENE IN RICE CONFERS BROAD-SPECTRUM RESISTANCE TO *XANTHOMONAS ORYZAE* PV. *ORYZAE* AND ENHANCED RESISTANCE TO *XANTHOMONAS ORYZAE* PV. *ORYZICOLA*

CROSS-REFERENCE TO RELATED APPLICATIONS

The present application is a national stage filing under 35 U.S.C. §371 of PCT/SG2008/000005, filed on 8 Jan. 2008 which in turn claims priority under 35 U.S.C. §119(e) to U.S. provisional patent application Ser. No. 60/897,864 filed 29 Jan. 2007, each of which is incorporated herein by reference.

BACKGROUND OF THE INVENTION

The present invention relates generally to plant molecular biology and genetic approaches for engineering enhanced and broad-spectrum resistance to bacterial diseases in plants.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Bacterial blight of rice (*Oryza sativa*) caused by *Xanthomonas oryzae* pv. *oryzae* is one of the most destructive bacterial diseases throughout the world (Mew, 1987). *X. oryzae* pv. *oryzae* enters susceptible cultivars via hydathodes, multiplies in the epithelium, and moves to the xylem vessels to cause systemic infection (Ronald, 1997). In resistant cultivars, reduced growth of the avirulent race is reflected in lower bacterial populations, reduced lesion development, activation of defense gene expression and changes of the cell wall and plasma membrane that are adjacent to avirulent bacterial cells (Young et al., 1996; Gu et al., 2005).

Bacterial leaf streak, another bacterial disease of rice caused by *Xanthomonas oryzae* pv. *oryzicola*, is an emerging problem in rice growing countries (Nino-Liu et al. 2006). *X. oryzae* pv. *oryzicola* penetrates the leaf mainly through stomata, multiplies in the substomatal cavity and then colonizes the intercellular spaces of the parenchyma (Nino-Liu et al. 2006). Like *X. oryzae* pv. *oryzae*, *X. oryzae* pv. *oryzicola* may also gain access through wounds, but it remains restricted to the apoplast of the mesophyll tissue and does not invade the xylem (Ou, 1985). *X. oryzae* pv. *oryzicola* exudes from natural openings in the leaf in chains or strands, or under moist conditions as small beads of ooze, which is a typical sign of bacterial leaf streak (Nino-Liu et al. 2006).

The use of resistant cultivars is the most economical and effective method to control bacterial blight disease (Ogawa, 1993). Race-specific interaction between rice and *X. oryzae* pv. *oryzae* is thought to follow the classic gene-for-gene concept (Flor, 1971). The products of plant resistance (R) gene recognize or interact with an elicitor molecule presumably encoded by an avirulence (Avr) gene from the pathogen, leading to the activation of a cascade of defense responses and effectively inhibit pathogen invasion. Currently, more than two dozen R genes or loci against *X. oryzae* pv. *oryzae* have been identified in rice, most of them providing complete, race-specific resistance (Kinoshita, 1995; Lin et al., 1996; Zhang et al., 1998; Khush and Angeles, 1999; Gao et al., 2001; Chen et al., 2002; Yang et al., 2003; He et al., 2006). Four dominant R genes, Xa21 (Song et al., 1995), Xa1 (Yoshimura et al., 1998), Xa26 (Sun et al., 2004) and Xa27 (Gu et al., 2005), and two recessive R genes, xa5 (Iyer and McCouch, 2004) and xa13 (Chu et al., 2006), have been isolated by map-based cloning.

Few studies have been conducted on control methods for bacterial leaf streak. As is the case for bacterial blight, in practice, host genetic resistance is the most important control measure for bacterial leaf streak, although it is so far limited to quantitative resistance (Gnanamanickam et al., 1999; Sheng et al., 2005; Tang et al., 2000).

Unlike other R genes isolated from dicots, the R genes for bacterial blight resistance isolated from rice encode products with great diversity. Xa21 and Xa26 encode receptor-like proteins (Song et al., 1995; Sun et al., 2004). Biochemical analysis of the putative kinase domain of Xa21 revealed that Xa21 encodes a functional serine threonine protein kinase capable of autophosphorylation on multiple sites (Liu et al., 2002). The Xa1 gene product contains nucleotide binding sites (NBS) and leucine-rich repeats (LRR) and is a member of the largest class of plant R proteins (Yoshimura et al., 1998). The xa5 gene encodes the gamma, subunit of transcriptional factor IIA (TFIIA), a eukaryotic transcriptional factor with no previously known role in disease resistance (Iyer and McCouch, 2004). The xa13 gene encodes an MtN3-like protein (Chu et al., 2006). The dominant allele of the gene presumably functions in both disease susceptibility and pollen development (Chu et al., 2006). The recently isolated Xa27 gene encodes a novel protein that has no apparent sequence homology to proteins from organisms other than rice (Gu et al., 2005).

Currently, five Avr genes have been isolated from *X. oryzae* pv. *oryzae* and all of them belong to the AvrBs3 family of type-III effectors. Four type-III effectors AvrXa3 (Li et al., 2004; Lee et al., 2005), AvrXa7 (Hopkins et al., 1992; Vera Cruz et al., 2000), AvrXa10 (Hopkins et al., 1992; Zhu et al., 1998) and avrXa27 (Gu et al., 2005) are recognized respectively by four cognate dominant R genes, Xa3, Xa7, Xa10 and Xa27, in the host. Given that Xa5 genotypes are susceptible to *X. oryzae* pv. *oryzae*, it is speculated that type-III effector Avrxa5 targets wild-type Xa5 for pathogenicity. The mutated protein xa5 cannot be targeted by Avrxa5 during pathogenesis, so the plant containing homozygous xa5 alleles were resistant or "non-susceptible" to *X. oryzae* pv. *oryzae* infection (Schornack et al., 2006).

Xa27 and avrXa27 are the first pair of R and Avr genes isolated from rice and *X. oryzae* pv. *oryzae*, respectively (Gu et al., 2005). avrXa27 is a member of the AvrBs3/PthA family of nuclear localized type-III effectors with 16.5 thirty-four amino acid direct repeats in the central repetitive domain and a conserved C-terminal region containing three nuclear localization signal (NLS) motifs and a transcription activation domain (AD). The central repetitive region determines the avrXa27-elicited resistance specificity while the NLS motifs and AD domain are required for Xa27-dependent elicitation and resistance. Unexpectedly, the resistant and susceptible parental lines of the Xa27 mapping population encode identical Xa27 proteins. The polymorphism of nucleotide sequences between the presumed Xa27/xa27 promoters raised the possibility that the two alleles differ in their expression. Indeed, only the Xa27 allele, but not the xa27 allele, was detected by Northern blot analysis. Further studies revealed that expression of the Xa27 allele occurs only when a rice plant is challenged by bacteria harboring avrXa27, but not the mutated isogenic strains lacking avrXa27. These data suggests that the resistance specificity of Xa27 towards incompatible pathogens involves the differential expression of the Xa27 allele in the presence of the avrXa27 effector.

The Avr gene has bifunctional signals in virulence and host recognition (Kjemtrup et al., 2000; Alfano et al., 2004; Yang et al., 2000). When an Avr gene performs its virulent function, it suppresses host defenses during pathogenesis in compatible interactions. However, when the Avr gene acts as an avirulent gene, it betrays the pathogen to plant defense by being recognized by the cognate host R gene and triggering hypersensitive response (HR) in incompatible interactions. The virulent function of several Avr proteins expressed in planta was found to cause suppression of host defenses, cell death or necrosis in plants lacking cognate R genes (Gopalan et al., 1996; McNellis et al., 1998; Duan et al., 1998; Chen et al., 2000; Chen et al., 2004; Hauck et al., 2003). In plants carrying specific R genes, the Avr proteins expressed in planta can elicit an HR or cause lethality (Gopalan et al., 1996; Scofield et al., 1996; Tang et al., 1996; Van den Ackerveken et al., 1996; de Feyter et al., 1998; McNellis et al., 1998; Stevens et al., 1998).

There is a need to develop methods of generating disease resistance in plants and in particular to methods of generating broad-spectrum resistance to bacterial blight and enhanced resistance to bacterial leaf streak.

SUMMARY OF THE INVENTION

The present invention generally provides a method to generate broad-spectrum resistance to bacterial blight disease and enhanced resistance to bacterial leaf streak in plants. More specifically, the present invention provides a method to generate broad-spectrum resistance to *Xanthomonas oryzae* pv. *oryzae*, the causal agent of bacterial blight disease of rice, and enhanced resistance to *Xanthomonas oryzae* pv. *oryzicola*, the causal agent of bacterial leaf streak of rice. Xa27, an inducible bacterial blight R gene in rice, was induced by the cognate avrXa27 gene expressed in host. Rice plants carrying the avrXa27 transgene and wild-type Xa27 gene conferred resistance to incompatible and compatible pathogens, and enhanced resistance to *X. oryzae* pv. *oryzicola* strain L8. The Xa27-mediated enhanced resistance to *X. oryzae* pv. *oryzicola* was also observed in the interaction between IRBB27 and L8 harboring pHM1avrXa27. This was further verified by the fact that the Xa27 gene in IRBB27 was induced by the avrXa27 gene in bacteria. The method can be used to engineer broad-spectrum resistance of rice to bacterial blight and enhanced resistance to bacterial leaf streak. Slight modification of this technique can be applied to control bacterial diseases in other crops.

Thus, in a first aspect, the present invention provides transgenic plants having the avrXa27 gene stably incorporated into their genome. In one embodiment, the avrXa27 gene is a wild-type gene isolated from *Xanthomonas oryzae* pv *oryzae*. In another embodiment, the avrXa27 gene has been modified. In another embodiment, the gene is an avrXa27-like type-III effector gene, which may be wild-type or modified. avrXa27 gene is used herein in the generic sense to refer to each of these embodiments, unless the context dictates otherwise.

In a second aspect, the present invention provides plants having the avrXa27 gene and the Xa27 gene. In one embodiment, such plants are produced by transforming plants containing the Xa27 gene with an avrXa27 gene. In another embodiment, such plants are produced by crossing plants containing the Xa27 gene with transgenic plants containing the avrXa27 gene. In one embodiment, the plants containing the Xa27 gene are native plants that contain the gene, either naturally or from conventional breeding. In another embodiment, the plants containing the Xa27 gene are transgenic plants for the Xa27 gene. The plants having the avrXa27 gene and the Xa27 gene have a broad spectrum resistance to both compatible and incompatible bacterial blight strains and enhanced resistance to bacterial leaf streak strains.

In a third aspect, the present invention provides a method of inducing expression of the Xa27 gene by expressing the avrXa27 gene in a plant. The avrXa27 gene is expressed in the plant under the control of a promoter. In one embodiment, the promoter is a constitutive promoter. In another embodiment, the promoter is an inducible promoter. In another embodiment, the promoter is a tissue specific promoter. The plant may be any of the plants described above.

In a fourth aspect, the present invention provides a method of generating enhanced and broad spectrum resistance to bacterial blight in plants. The method comprises expressing the avrXa27 gene in a plant containing the Xa27 gene in which the expression of the avrXa27 gene induces expression of the Xa27 gene. In one embodiment, the avrXa27 gene is expressed prior to infection by the causative pathogen. In another embodiment, the avrXa27 gene is expressed after the plant has been infected. The plant may be any of the plants described above.

In a fifth aspect, the present invention provides a method of generating enhanced resistance to bacterial leaf streak in plants. The method comprises expressing the avrXa27 gene in a plant containing the Xa27 gene in which the expression of the avrXa27 gene induces expression of the Xa27 gene. In one embodiment, the avrXa27 gene is expressed prior to infection by the causative pathogen. In another embodiment, the avrXa27 gene is expressed after the plant has been infected. The plant may be any of the plants described above.

The plants in accordance with the present invention may be rice, pepper, tomato, beans, cotton, cucumber, cabbage, barley, oats, wheat, corn and citrus.

BRIEF DESCRIPTION OF THE FIGURES

FIG. 4a: Expression of Xa27 in the $F_1$ plants derived from the crosses between IRBB27 and different transgenic plants (L24, L1, L14 and L25). In both experiments, about 5 μg of mRNA was loaded on each lane and expression of rice ubiquitin gene 2 (Ubi) was used as a loading control. Northern blot was probed with $^{32}$P-labelled full-length Xa27 cDNA. The control line was derived from transformation of Nipponbare with pC1305.1. FIG. 4b: Xa27 but not xa27 was specifically induced by the avrXa27 transgene from L24.

FIG. 6a: Disease phenotype of bacterial leaf streak on leaves of the $BC_3F_1$ plants of IRBB27×Control line, IR24×L24 and IRBB27×L24 at 10 days after inoculation with X. oryzae pv. oryzicola strain L8. The Control line was derived from transformation of Nipponbare with pC1305.1. FIG. 6b: Bacterial population of X. oryzae pv. oryzicola strain L8 in leaves of the $BC_3F_1$ plants of IRBB27×Control line, IR24×L24 and IRBB27×L24 over 10 days by syringe infiltration. FIG. 6c: Disease phenotype of bacterial leaf streak on leaves of IRBB27 plants at 3 (Leaves 1 and 2) and 10 (leaves 3 and 4) days after inoculation with X. oryzae pv. oryzicola strains L8(pHM1) (leaves 1 and 3) and L8(pHM1avrXa27) (leaves 2 and 4). FIG. 6d: Bacterial population of X. oryzae pv. oryzicola strains L8(pHM1) and L8(pHM1avrXa27) in leaves of the IRBB27 plants over 10 days by syringe infiltration. FIG. 6e: Induction of Xa27 in leaves of IRBB27 plants by X. oryzae pv. oryzicola strains L8(pHM1) and L8(pHM1avrXa27). Lane 1, IRBB27 infiltrated by L8(pHM1) at 0 day after syringe infiltration; Lane 2, IRBB27 infiltrated by L8(pHM1avrXa27) at 0 day after syringe infiltration; Lane 3, IRBB27 infiltrated by L8(pHM1) at 3 days after syringe infiltration; Lane 4, IRBB27 infiltrated by L8(pHM1avrXa27) at 3 days after syringe infiltration.

DETAILED DESCRIPTION OF THE INVENTION

Figure 1:
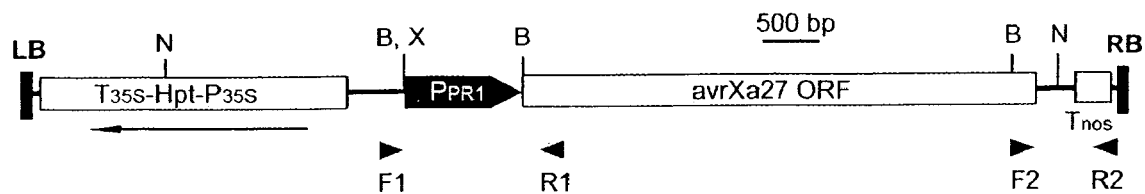
FIG. 1 shows a schematic map of T-DNA region of pCPR1avrXa27. The arrow indicates the direction of transcription of Hpt gene. LB, left border; RB, right border; $T_{35S}$, terminator of cauliflower mosaic virus (CaMV) 35S gene; $P_{35S}$, promoter of CaMV 35S gene; $P_{PR1}$, promoter of rice PR1 gene; avrXa27 ORF, coding region of avrXa27 from *Xanthomonas oryzae* pv. *oryzae* PXO99$^A$; $T_{nos}$, terminator of nopaline synthase (nos) gene. B, BamH I; N, Nde I; X, Xba I. F1, forward primer for PR1 promoter; R1, reverse primer for PR1 promoter; F2, forward primer for $T_{nos}$; R2, reverse primer for $T_{nos}$.
Figure 2:
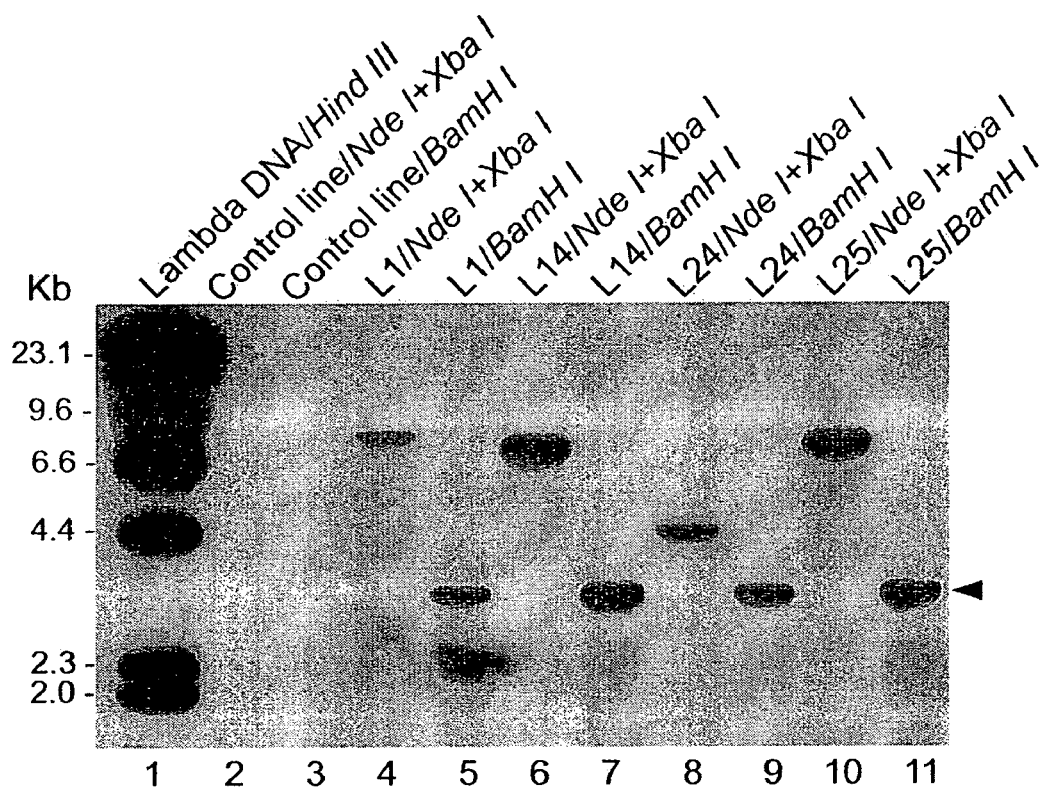
FIG. 2 shows the molecular analysis of transgenic avrXa27 plants. Two to five micrograms of DNA isolated from transgenic plants (L1, L14, L24 and L25) as well as from control plant were digested with restriction enzymes Nde I and Xba I, or BamH I only. Southern blot was probed with $^{32}$P-labelled 3234-bp BamH I fragment from avrXa27. Arrow indicates the position of BamH I fragment of the avrXa27 coding region in pCPR1avrXa27. The control line was derived from transformation of Nipponbare with pC1305.1.
Figure 3:
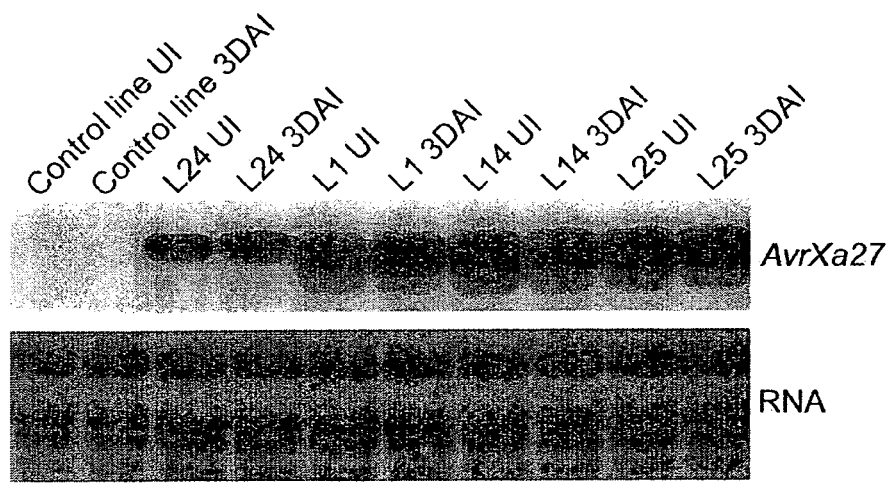
FIG. 3 shows the expression of the avrXa27 transgenes in transgenic plants. Four selected avrXa27 transgenic plants (L24, L1, L14 and L25) as well as the control plants were subjected for northern blot analysis. Total RNAs were isolated from un-inoculated plants (UI) or plants at 3 day after inoculation (3DAI) with *X. oryzae* pv. *oryzae* strain PXO99$^A$. About 30 µg of total RNA was loaded to each lane. The RNA loading was assessed by staining RNA blots with methylene blue. Northern blot was probed with $^{32}$P-labelled 3234-bp BamH I fragment from avrXa27. The control line was derived from transformation of Nipponbare with pC1305.1.

Race-specific resistance of plants to pathogenic bacteria is controlled by resistance (R) genes in host and cognate avirulence (Avr) genes in pathogens. The present invention generally provides a method to generate broad-spectrum resistance to bacterial blight disease in plants. The present invention also generally provides a method to generate enhanced resistance to bacterial leaf streak in plants. More specifically, the present invention provides a method to generate broad-spectrum resistance to Xanthomonas oryzae pv. oryzae, the causal agent of bacterial blight disease in rice, and enhanced resistance to Xanthomonas oryzae pv. oryzicola, the causal agent of bacterial leaf streak of rice. Xa27, an inducible bacterial blight R gene in rice, is induced by the cognate avrXa27 gene expressed in a host plant. Rice plants carrying avrXa27 transgene and wild-type Xa27 gene conferred resistance to incompatible and compatible pathogens and enhanced resistance to X. oryzae pv. oryzicola strain L8. The method can be used to engineer broad-spectrum resistance to bacterial blight disease in rice. Slight modification of this technique is applied to control bacterial diseases in other crops.

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

In an embodiment of the present invention, stable transgenic avrXa27 lines were generated by Agrobacterium-mediated transformation. Stable transgenic lines also were prepared using the DNA constructs described herein and techniques well known to the skilled artisan. The expression of the avrXa27 gene in transgenic lines did not cause obvious HR or other visible stress phenotypes in Nipponbare lacking Xa27. Constitutive induction of the Xa27 gene in the $F_1$ plants from the crosses between IRBB27 (Xa27/Xa27) and the transgenic avrXa27 lines was revealed by Northern analysis. Even though avrXa27 proteins in transgenic lines were not detected in immunoblot analysis, the $F_1$ plants nevertheless showed high resistance to incompatible and compatible pathogens. The Xa27 gene is a dominant resistance gene in IR24 genetic background. However, it may be a semi-dominant resistance gene in other rice genetic background, such as CO39 (Gu et al., 2004). Xa27 also showed moderate resistance to bacterial blight or semi-dominant phenotype in the $F_1$ plants derived from a cross between IRBB27 and Nipponbare. The present invention provides a new approach to generate enhanced or complete resistance of the Xa27 gene to bacterial blight in the $F_1$ plants derived from a cross between IRBB27 and Nipponbare as well in other plants. Even though the Xa27 gene conferred broad-spectrum resistance to multiple X. oryzae pv. oryzae strains, the IRBB27 plants were still susceptible to 5 compatible X. oryzae pv. oryzae strains (Gu et al., 2004). The present invention provides a new approach to generate enhanced resistance to those compatible X. oryzae pv. oryzae strains and, therefore, the engineered rice plants had broader resistance spectrum than that of the IRBB27 plants. In addition, the present invention provides a new approach to generate enhanced resistance to bacterial leaf streak X. oryzae pv. oryzicola and, therefore, the engineered rice plants had an enhanced resistance compared to that of the parent plants. In conclusion, the present invention provides a new approach to generate enhanced and broad-spectrum resistance to bacterial blight disease in rice and other plants, as well as a new approach to generate enhanced resistance to bacterial leaf streak in rice and other plants.

More specifically, methods of the invention involve stably transforming a plant with an avirulence gene, specifically a nucleic acid encoding an avrXa27 protein, operably linked with a promoter capable of driving expression of a gene in a plant cell. A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom. Expression of the avirulence gene induces the Xa27 gene, which provides broad spectrum and enhanced resistance to compatible and incompatible pathogens, specifically Xanthomonas species.

In one embodiment, the avrXa27 protein has the amino acid sequence set forth in SEQ ID NO:2 (GenBank Accession No. AAY54168). The avrXa27 protein, when expressed in a plant containing the Xa27 resistance gene provides broad spectrum resistance to bacterial blight disease and enhanced resistance to bacterial leaf streak.

In an additional embodiment, the avrXa27 protein may be modified or may be an active fragment. "Protein modifications or fragments" as used herein are substantially homologous to primary structural sequence but which include, e.g., in vivo or in vitro chemical and biochemical modifications or which incorporate unusual amino acids, generally without affecting the biological activity of the protein. Such modifications include, for example, acetylation, carboxylation, phosphorylation, glycosylation, ubiquitination, labeling, e.g., with radionuclides, and various enzymatic modifications, as will be readily appreciated by persons of ordinary skill in the art. For convenience, the avrXa27 protein (or corresponding gene) will be used for descriptive purposes herein. However, it will be understood that the protein (or corresponding gene) may refer to the wild-type or modified avrXa27 protein (or gene).

Other protein modifications include amino acid substitution. Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known to persons of ordinary skill in the art and typically include, though not exclusively, substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with a polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art. Alternatively, the substitution of like amino acids can be made effectively on the basis of hydrophilicity. The importance of hydrophilicity in conferring interactive biological function of a protein is generally understood in the art (see e.g., U.S. Pat. No. 4,554,101). The use of the hydrophobic index or hydrophilicity in designing polypeptides is further discussed in U.S. Pat. No. 5,691,198.

The present invention also provides for fusion polypeptides, comprising avrXa27 polypeptides and fragments thereof and polypeptides or fragments of other proteins as known in the art. Homologous polypeptides may be fusions between two or more polypeptide sequences or between the sequences of avrXa27 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding and may include for example partners such as FLAG epitopes, immunoglobulins, bacterial β-galactosidase, trpE, protein A, β-lactamase, alpha amylase, alcohol dehydrogenase and yeast alpha mating factor.

The polynucleotide compositions of this invention include RNA, cDNA, genomic DNA, synthetic forms, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The polynucleotides of the invention may be isolated or substantially pure. An "isolated" or "substantially pure" nucleic acid or polypeptide is one which is substantially separated from other cellular components which naturally accompany a native sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

In one embodiment, a nucleic acid encoding an avrXa27 protein has the nucleic acid sequence set forth in SEQ ID NO:1 (GenBank Accession No. AY986494). Other nucleic acid sequences which encode this protein, such as nucleic acids resulting from the degeneracy of the genetic code, are also contemplated. In addition, nucleic acid sequences encoding the modified proteins are also contemplated.

Where appropriate, the avirulence sequence and any additional gene(s) may be optimized for increased expression in the transformed plant. That is, these nucleotide sequences can be synthesized using plant-preferred codons for improved expression. Methods are available in the art for synthesizing plant-preferred genes. See, for example, U.S. Pat. No. 5,380,831, U.S. Pat. No. 5,436,391, and Murray et al. (1989), each incorporated herein by reference.

The nucleotide sequences for the avirulence gene of the present invention are useful in the genetic manipulation of any plant when operably linked to a promoter and/or other regulatory sequences that are functional within the plant. The term "promoter" or "regulatory element" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention. "Regulatory sequences"

refers to those sequences which affect the expression of the gene (including transcription of the gene, and translation, splicing, stability or the like of the messenger RNA). By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

In this manner, the nucleotide sequences of the invention are provided in expression cassettes for expression in the plant of interest. An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. A "construct" is a nucleic acid molecule that is isolated from a naturally occurring gene or which has been modified to contain segments of nucleic acid which are combined and juxtaposed in a manner which would not otherwise exist in nature. Such expression cassettes will include 5' and 3' regulatory sequences operably linked to an avirulence gene sequence of the invention. The cassette may additionally contain at least one additional gene to be cotransformed into the organism. Alternatively, the additional gene(s) can be provided on multiple expression cassettes.

Typically, the expression cassette will include in the 5'-3' direction of transcription, a transcriptional and translational initiation region, an avirulence gene sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced or alternatively is found after transformation at a different site in the genome. As used herein, a chimeric gene comprises a coding sequence operably linked to a transcription initiation region that is heterologous to the coding sequence.

A number of promoters can be used in the practice of the invention, including constitutive, inducible, pathogen-inducible, wound-inducible, and tissue-specific promoters. See, e.g., U.S. Pat. No. 7,109,397. For example, for overexpression, a plant promoter fragment may be employed which will direct expression of the gene in all tissues of a regenerated plant. Such promoters are referred to herein as "constitutive" promoters and are active under most environmental conditions and states of development or cell differentiation.

Examples of some constitutive promoters that are widely used for inducing expression of transgenes include, without limitation, the nopoline synthase (NOS) gene promoter from *Agrobacterium tumefaciens* (U.S. Pat. No. 5,034,322), the cauliflower mosaic virus (CMV) 35S and 19S promoters (U.S. Pat. No. 5,352,605), those derived from any of the several actin genes, which are known to be expressed in most cells types (U.S. Pat. No. 6,002,068), the ubiquitin promoter, which is a gene product known to accumulate in many cell types, the enhanced 35S promoter (U.S. Pat. No. 5,106,739), the dual 35S promoter, the FMV promoter from figwort mosaic virus (U.S. Pat. No. 5,378,619), the RI T-DNA promoter (U.S. Pat. No. 5,466,792), the octopine T-DNA promoter (U.S. Pat. No. 5,428,147), the alcohol dehydrogenase 1 promoter (Callis et al., 1987), the patatin promoter B33 (Rocha-Sosa et al., 1989), the E8 promoter (Deikman and Fishcer, 1988), the beta-conglycin promoter (Tierney et al., 1987), the acid chitinase promoter (Samac et al., 1990), the *Arabidopsis* histone H4 promoter (U.S. Pat. No. 5,491,288), or the recombinant promoter for expression of genes in monocots (U.S. Pat. No. 5,290,924). Additional constitutive regulatory elements including those for efficient expression in monocots also are known in the art, for example, the pEmu promoter and promoters based on the rice Actin-1 5' region (Last et al., 1991; McElroy et al., 1991; McElroy et al., 1990).

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an inducible promoter system used the XVE transcriptional factor (U.S. Pat. No. 6,784,340). Another example of an inducible promoter is a pathogen-inducible promoter. Such promoters include those from pathogenesis-related proteins (e.g., PR proteins, SAR proteins, beta-1,3-glucanase, chitinase), which are induced following infection by a pathogen (see, e.g., Redolfi et al., 1983; Uknes et al., 1992; and Van Loon, 1985). In one embodiment, the promoter is the promoter of the rice PR1 gene (Gu et al., 2005; SEQ ID NO:13).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu, 1997); the auxin-responsive *Arabidopsis* GST6 promoter (also responsive to salicylic acid and hydrogen peroxide) (Chen et al., 1996); the auxin-inducible parC promoter from tobacco (Sakai et al., 1996); a plant biotin response element (Streit and Phillips, 1997); and, the promoter responsive to the stress hormone abscisic acid (Sheen, 1996).

In addition, inducible promoters include promoters that function in a tissue specific manner to regulate the gene of interest within selected tissues of the plant. Examples of tissue-specific promoters under developmental control include promoters that initiate transcription only in certain tissues, such as fruit, seeds, roots, or flowers. Examples of such tissue specific promoters are well known in the field (U.S. Pat. No. 5,750,385) and include the H4A748 promoter expressed in shoot meristems (Atanassova et al., 1992). RCc2 and RCc3 promoters that direct root-specific gene transcription in rice (Xu et al., 1995).

Thus the expression cassette will include in the 5'-3' direction of transcription, a transcriptional and translational initiation region, a nucleotide sequence encoding the avirulence protein of the present invention, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991); Proudfoot (1991); Sanfacon et al. (1991); Mogen et al. (1990); Munroe and Jacobson (1990); Joshi (1987).

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al., 1989); potyvirus leaders, for example, TEV leader (Tobacco Etch Virus) (Allison et al., 1986); and human immunoglobulin heavy-chain binding protein (BiP), (Macejak and Sarnow, 1991); untranslated leader from the coat protein mRNA of alfalfa mosaic virus (AMV RNA 4) (Jobling and Gehrke, 1987); tobacco mosaic virus leader (TMV) (Gallie et al., 1989); and maize chlorotic mottle virus leader (MCMV) (Lommel et al., 1991). See also, Della-Cioppa et al. (1987). Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta. Any scorable or screenable marker gene can be used in a transient assay. Preferred marker genes for transient analyses of the promoters or promoter fragments of the present invention include a GUS gene (U.S. Pat. No. 5,599,670) or a GFP gene (U.S. Pat. No. 5,491,084). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Once a nucleic acid has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

DNA constructs containing an avirulence sequence of the present invention can be used to transform any plant and may be introduced into the genome of the desired plant host by a variety of conventional techniques. Techniques for transforming a wide variety of higher plant species are well known and described in the technical and scientific literature. See, for example, Weising et al., 1988. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. (1984). Electroporation techniques are described in Fromm et al. (1985) and U.S. Pat. No. 5,384,253. Microprojectile bombardment techniques are described in Klein et al. (1987); Tomes et al. (1995); U.S. Pat. No. 4,945,050; U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865.

*Agrobacterium tumefaciens*-mediated transformation techniques, including disarming and use of binary vectors, are well described in the scientific literature. See, for example Horsch et al. (1984); Fraley et al. (1983); U.S. Pat. No. 5,563,055; U.S. Pat. No. 5,824,877; U.S. Pat. No. 5,591,616; U.S. Pat. No. 5,981,840; U.S. Pat. No. 6,384,301; and, U.S. Pat. No. 7,112,721.

Transformed plant cells which are derived by any of the above transformation techniques can be cultured to regenerate a whole plant which possesses the transformed genotype and thus the desired phenotype, e.g., a transgenic plant. A "transgenic plant" is an plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al. (1983); Binding (1985); Vasil (1984); and Vasil (1986). Regeneration can also be obtained from plant callus, explants, organs, or parts thereof. Such regeneration techniques are described generally in Klee et al. (1987). It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants.

In accordance with the present invention, transgenic plants are produced that contain the avrXa27 gene. In one embodiment, the transgenic plants are produced by transforming rice plant cells with the avrXa27 gene as described herein. In one aspect, the rice plant cells that are transformed do not contain the Xa27 gene. In a second aspect, the rice plant cells that are transformed may contain the Xa27 gene, such that transgenic plants are obtained that contain both the avrXa27 gene and the Xa27 gene. The rice plant cells that contain the Xa27 gene may be derived from rice varieties that naturally contain the Xa27 gene or that have been stably transformed in accordance with the principles described herein to contain the Xa27 gene. The Xa27 protein is set forth in SEQ ID NO:4 and one embodiment of the Xa27 gene is set forth in SEQ ID NO:3. Other nucleic acid sequences which encode the Xa27 proteins, such as nucleic acids resulting from the degeneracy of the genetic code, are also contemplated. As with the avrXa27 protein, the Xa27 protein can be a modified protein as long as it retains its activity. Protein modifications include those described herein with reference to the avrXa27 protein. Nucleic acid sequences encoding the modified proteins are also contemplated.

In accordance with the present invention, plants are provided having the avrXa27 gene and the Xa27 gene. In one embodiment, the plants are transgenic plants that contain both genes. In one aspect, the transgenic plant is produced by simultaneously transforming a plant with the avrXa27 gene and the Xa27 gene using techniques such as those described herein. In another aspect, the transgenic plant is produced by first transforming a plant with either the avrXa27 gene or Xa27 gene using techniques such as those described herein, and then transforming this transgenic plant with the other gene using techniques such as those described herein. In another embodiment, the plants are plants produced by crossing plants containing the Xa27 gene with transgenic plants containing the avrXa27 gene using conventional plant breeding techniques. In one embodiment, the plants containing the Xa27 gene are native plants that contain the gene, either naturally or from conventional breeding. In another embodiment, the plants are transgenic plants containing the Xa27 gene. These plants have a broad spectrum resistance to both compatible and incompatible bacterial strains that are causative agents for bacterial blight disease. These plants also have an enhanced resistance to bacterial leaf streak In accordance with the present invention, a method is provided to induce expression of an Xa27 gene by expressing an avrXa27 gene in a plant. In one embodiment, the avrXa27 gene is expressed in a plant that also contains the Xa27 gene. The plant may be a transgenic plant or may be produced by conventional breeding. The avrXa27 gene is expressed in the plant under the control of a promoter as described herein. In one embodiment, the promoter is a constitutive promoter, in which instance the avrXa27 gene is expressed at all times during the growth of the plant. In another embodiment, the promoter is an inducible promoter, in which instance avrXa27 gene expression is induced by the presence of the inducer in the plant during the growth of the plant. In another embodiment, the promoter is a tissue specific promoter, in which instance the avrXa27 gene expression is limited to the tissue in which the promoter is active during the growth of the plant.

Also in accordance with the present invention, a method is provided to generate an enhanced and broad spectrum resistance to bacterial blight in plants and enhanced resistance to bacterial leaf streak. The method comprises expressing the avrXa27 gene in a plant containing the Xa27 gene in which the expression of the avrXa27 gene induces expression of the Xa27 gene. In one embodiment, the avrXa27 gene is expressed prior to infection by the causative pathogen. In another embodiment, the avrXa27 gene is expressed after the plant has been infected. The expression of the avrXa27 gene may be constitutive, induced or tissue specific. If expression is constitutive, the avrXa27 gene is expressed at all times during the growth of the plant. If expression is induced, the avrXa27 gene expression is induced by the presence of the inducer in the plant during the growth of the plant. If expression is tissue specific, the avrXa27 gene expression is limited to the tissue in which the promoter is active during the growth of the plant. The expression of the Xa27 gene resulting from the expression of the avrXa27 gene produces a broad spectrum resistance to bacterial blight caused by both compatible and incompatible strains of the pathogens. The expression of the Xa27 gene resulting from the expression of the avrXa27 gene produces also produces an enhanced resistance to bacterial leaf streak.

Slight modification of the technique described herein is applied to control bacterial diseases in other plants, including but not limited to, pepper, tomato, beans, cotton, cucumber, cabbage, barley, oats, wheat, corn and citrus. Members of AvrBs3/PthA family of type-III effectors are, with one exception (Brg11 from *Ralstonia solanacearum*) (Cunnac et al., 2004), exclusively found in *Xanthomonas* spp (Lahaye and Bonas, 2001). The avirulence activity of AvrBs3 (Bonas et al., 1989) from *X. campestris* pv. *vesicatoria* (a pepper and tomato pathogen), PthA (Swamp et al., 1991) from *X. axonopodis* pv. *citri* (a citrus pathogen), Avrb6 (De Feyter and Gabriel, 1991) from *X. campestris* pv. *malvacearum* (a cotton pathogen) and AvrXa7 or AvrXa10 (Hopkins et al., 1992) from *X. oryzae* pv. *oryzae* (a rice pathogen) elicit the HR and resistance in resistant plants that carry the corresponding R genes. Expression of those avirulence effectors in host plants will elicit R gene-mediated resistance to these pathogenic bacteria. One thing that should be noted is that some members of the AvrBs3/PthA family not only display an avirulence activity but also contribute to the virulence of bacteria (Swamp et al., 1991; Yang et al., 1996; Bai et al., 2000; Marois et al., 2002). Therefore, an inducible promoter (for instance, a pathogen inducible promoter) should be used to control the expression of these Avr genes in plant hosts that carry the corresponding R genes.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, New. York); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Plasmids, Bacterial Strains and Growth Conditions

Plasmids used in this study were cosmids 99-avrXa27-20 (Gu et al., 2005) and pHM1avrXa27, cloning vector pGEM-T-easy (Promega, Wis. 53711, USA) and plant transformation vector pC1305.1 (CAMBIA, Canberra, Australia) and pCPR1avrXa27 (preparation described herein). Bacterial strains used in this study were *Escherichia coli* strain DH10b (Carlsbad, Calif. 92008, USA), *Agrobacterium tumefaciens* strain AGL1 (Lazo et al., 1991), *X. oryzae* pv. *oryzae* strains PXO99$^4$, AXO1947, AXO1947(pHM1 avrXa27), K202, ZHE173 and CIAT1185 and *X. oryzae* pv *oryzicola* strains L8(pHM1) and L8(pHM1avrXa27). *Escherichia coli* was cultivated at 37° C. in Luria-Bertani medium, *A. tumefaciens* strains at 28° C. in YEB medium, *X. oryzae* pv. *oryzae* and *X. oryzae* pv. *oryzicola* strains at 28° C. in PSA medium (Gu et al., 2004). Plasmids were introduced into *E. coli, A. tumefaciens, X. oryzae* pv. *oryzae* or *X. oryzae* pv. *oryzicola* strains by electroporation (Sambrook et al., 1989).

Plant Materials and Growth Conditions

Rice lines used in this study were Xa27 near-isogenic line IRBB27 (Gu et al., 2004) and cultivar Nipponbare. Rice plants, including those inoculated with *X. oryzae* pv. *oryzae* or *X. oryzae* pv. *oryzicola* strains, were grown in the greenhouse at a temperature of 26° C. (night) to 32° C. (day).

Plant Transformation

*Agrobacterium*-mediated transformation of Nipponbare was carried out according to the method described previously (Yin and Wang, 2000). Briefly, vigorously growing embryogenic calli derived from the scutellum of mature embryos was co-cultivated with *Agrobacterium tumefaciens* strain AGL1 harboring pCPR1avrXa27. After co-cultivation, the rice tissues were cultured on the NB$_o$ medium containing 250 mg/L cefotaxime, 200 mg/L ampicillin, 2 mg/L 2,4-D (2,4-dichlorophenoxy acetic acid) and 50 mg/L hygromycin at 26° C. in the dark for 3-4 weeks. Hygromycin-resistant calli were subcultured on fresh selection medium for 2 weeks and then transferred to the NB$_o$ medium containing 1 mg/L 6-benzylaminopurine (6-BA), 2 mg/L naphthaleneacetic acid (NAA), 5 mg/L abscisic acid (ABA) and 50 mg/L hygromycin for 2-3 weeks. Compact, white embryogenic calli showing hygromycin resistance were transferred to the NB$_o$ medium containing 2 mg/L 6-BA, 1 mg/L indoleacetic acid (IAA), 1 mg/L NAA, 1 mg/L KT (kinetin) and 50 mg/L hygromycin and grown at 26° C. with a 14-hour light and a 10-hour dark period. Regenerated plantlets were subsequently transplanted to the soil in pots and grown in a greenhouse.

Bacterial Blight Inoculation

Bacterial blight inoculation was carried out using the leaf-clipping method (Kauffman et al., 1973). Briefly, *X. oryzae* pv. *oryzae* strains were grown on PSA medium (10 g/L peptone, 10 g/L sucrose, 1 g/L glutamic acid, 16 g/L bacto-agar and pH 7.0) for 2-3 days. The bacterial cells were suspended in sterile water with a density of 0.5 at OD$_{600}$. The bacterial cell suspension was applied to the two youngest fully expanded leaves of each tiller by clipping 5-6 cm from the tip of the leaf using a pair of scissors dipped in the inoculum. Lesion length (LL) was measured two weeks after inoculation. The symptom of disease was ranked as resistant (R, LL≦3.0 cm), moderately resistant (MR, 3.0 cm≦LL≦6.0 cm), moderately susceptible (MS, 6.0 cm≦LL≦9.0 cm) and susceptible (S, LL>9.0 cm) (Amante-Bordeos et al., 1992).

Bacterial Leaf Streak Inoculation

For bacterial leaf streak inoculation, *X. oryzae* pv. *oryzicola* strain L8, L8(pHM1) or L8(pHM1avrXa27) were grown on PSA medium with appropriate antibiotics for 2-3 days. The bacterial cells suspended with sterile water with a density of 0.5 at OD$_{600}$. Rice plants were inoculated at six weeks after sowing by infiltration of leaves with bacterial suspension using needleless syringe (Schaad et al., 1996). The bacterial populations in inoculated plants were determined using the method reported by Makino et al. (2006) with slight modification. In brief, infiltrated areas of rice leaves were removed and grounded in 5 ml sterile water. Serial dilutions were made and spread on PSA agar plates with appropriate antibiotics. Plates were incubated at 28° C. until single colonies could be counted. The number of CFU per leaf was then estimated, and standard deviation was calculated using colony counts from repeat experiments. Experiments were repeated five times.

Southern Blot Analysis

Rice genomic DNA was extracted from leaves (Dellaporta et al., 1984). Approximately 2 µg of rice DNA was digested with an appropriate restriction enzyme and fractionated in a 0.65-0.8% agarose gel by electrophoresis. Southern blot analysis was carried out according to the standard procedures (Sambrook et al., 1989). Labelling of the probes and signal detection were done with the Rediprime™ II from Amersham Biosciences.

Northern Blot Analysis

Total RNA was isolated from rice leaves using RNeasy Plant Mini Kit from QIAGEN. About 20 µg total RNA of each sample was used for Northern blot analysis. Northern blot analysis was done according to the standard procedures (Sambrook et al., 1989). The RNA loading was assessed by ethidium bromide (EtBr) staining or by hybridization to the rice Ubiquitin I (Ubi) gene. Labelling of the probes and signal detection were done as described above.

Example 2

Construction of pCPR1 avrXa27 pCPR1avrXa27 was made based on CAMBIA vector pC1305.1. A 3482-bp genomic clone of the avrXa27 gene, including the 3411-bp full-length coding sequence (SEQ ID NO:5), was subcloned from cosmid 99-avrXa27-20 (Gu et al., 2005) into pGEM-T-easy vector (Promega) to create the intermediate construct pTavrXa27. The 3234-bp BamHI fragment of the avrXa27 gene in pTavrXa27 was replaced with the BamHI fragment of the avrXa27F2H gene from pZWavrXa27 (Gu et al., 2005) to create pTZWavrXa27. The SacII-AseI fragment from pTZWavrXa27 (containing the avrXa27 gene (SEQ ID NO:1)) was isolated, blunted and cloned to the downstream of rice PR1 promoter (Gu et al., 2005; SEQ ID NO:5) in pC1305.1 to generate pCPR1avrXa27 (FIG. 1). The primer pairs used to determine the presence of the PR1 promoter and the terminator of nopaline synthase gene (Tnos) in transgenic plants were PF/PR (5'-CCATGATTACGAATTCGAGCTCGG-'3 (SEQ ID NO:6) and 5'-AAGAAGCGACGGAT CGAACTGAC-3' (SEQ ID NO:7)) and TF/TR (5'-CGAAGAGGAGCTCG-CATGGTTGAT-3' (SEQ ID NO:8) and 5'-CACTGATAGTT-TAATTCCCGATCTAG-3' (SEQ ID NO:9)), respectively.

Example 3

Production of Transgenic avrXa27 Plants

The transgenic avrXa27 plants were produced by *Agrobacterium*-mediated transformation of cultivar Nipponbare with binary plasmid pCPR1avrXa27 (FIG. 1). pCPR1avrXa27 carries a $P_{PR1}$-avrXa27-Tnos fusion gene in its T-DNA region. Totally, thirty-four independent transgenic $T_0$ plants were generated. However, after molecular analysis, only four $T_0$ plants (lines L1, L14, L24 and L25) were found to carry intact avrXa27 gene. A 3.2-kb band corresponding to the expected BamH I fragment of the avrXa27 coding region (FIG. 1) was detected in southern blot analysis in all of the four transgenic plants (FIG. 2, lanes 5, 7, 9 and 11). A 4.5-kb band corresponding to the expected Nde I-Xba I fragment that comprised PR1 promoter and avrXa27 coding region (FIG. 1) was detected in L24 (FIG. 2, lane 8). However, the 4.5-kb Nde I-Xba 1 band was not detected in L1, L14 and L25. Instead, they all carried an Nde I-Xba I band with molecular size larger than 4.5 kb (FIG. 2, lanes 4, 6 and 10). To further characterize the avrXa27 gene in these transgenic plants, we isolated the 5' promoter and 3' terminator regions of the $P_{PR1}$-avrXa27-Tnos fusion gene by PCR with primer pairs F1/R1 and F2/R2, respectively. DNA sequences of the amplified PCR products showed that L24 carried the intact 5' promoter and 3' terminator. L1, L14 and L25 also contained intact 3' terminator region. However, they all underwent minor mutation for only several base pairs at the 5' end of PR1 promoter, which resulted in loss of the XbaI site. The morphology of these transgenic avrXa27 plants was similar to that of non-transgenic Nipponbare or control line generated from transformation with empty vector pC1305.1. The transgenic avrXa27 plants were selfed and the homozygous progeny were chosen for further studies.

Example 4

Expression of the avrXa27 Gene in Transgenic Plants

Northern blot analysis indicated that the avrXa27 transgenes in L1, L14, L24 and L25 expressed constitutively (FIG. 3). There was no significant difference in avrXa27 expression between un-inoculated (UI) plants and plants inoculated with *X. oryzae* pv. *oryzae* strain $PXO99^A$ at 3 days after inoculation (3DAI). The full-length avrXa27 transcripts were detected as a hybridized band at about 4 kb in northern blot analysis. The transgenic avrXa27 lines and the control line was used as pollen donors to cross with IRBB27, a near-isogenic line in IR24 background, and IR24, respectively.

Example 5

Disease Evaluation of L24 for Resistance to Bacterial Blight

To test whether the avrXa27 gene in rice has virulent and/or avirulent function, we inoculated homozygous $T_2$ plants of L24 with 5 compatible and 1 incompatible *X. oryzae* pv. *oryzae* strains. Expression of the avrXa27 gene in Nipponbare did not show any virulent function upon bacterial infection. On the contrary, the bacterial blight lesions on the L24 $T_2$ plants were slightly shorter than that on untransformed wild-type plants in the five compatible interactions and 1 incompatible interaction (Table 1). The data indicate that the avrXa27 gene in host has no or very weak virulent function to *X. oryzae* pv. *oryzae* pathogenesis.

TABLE 1

The avrXa27 Transgene in Nipponbare Did Not Show Any Virulent Function
for Either Compatible or Incompatible *X. oryzae* pv. *oryzae* Strains[a]
Lesion Length (cm) and Resistance Score[b]

| Lines | PXO99A | AXO1947 | AXO1947 (pHM1avrXa27) | K202 | ZHE173 | CIAT1185 |
|---|---|---|---|---|---|---|
| Nipponbare | 20.8 ± 4.7(S) | 24.5 ± 8.3(S) | 18.9 ± 4.2(S) | 18.9 ± 4.2(S) | 15.6 ± 4(S) | 4.7 ± 2.5(MR) |
| L24 | 20 ± 2.4(S) | 19.7 ± 3(S) | 16.9 ± 2.5(S) | 16.5 ± 3.1(S) | 14 ± 3.2(S) | 3.7 ± 2.5(MR) |

[a]Six-weeks-old plants were inoculated with *X. oryzae* pv. *oryzae*. For each *X. oryzae* pv. *oryzae* strain, at least sixteen leaves from four individual plants were inoculated. The lesion length is the average of 16 infected leaves. The standard deviation of the mean is indicated.
[b]Standard deviation of resistance scores in parentheses. R, resistant, 0 cm ≦ lesion length ≦ 3.0 cm; MR, moderately resistant, 3.0 cm < lesion length ≦ 6.0 cm; MS, moderately susceptible, 6.0 cm < lesion length ≦ 9.0 cm; S, susceptible, lesion length > 9.0 cm.

Example 6

Induction of the Xa27 Gene by the avrXa27 Transgene in Rice

Figure 4:
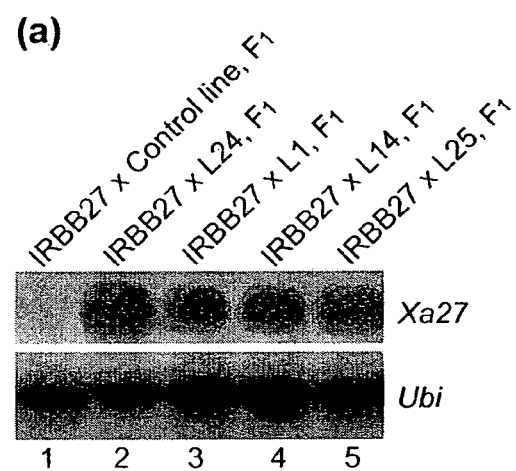
FIGS. 4a and 4b shows the specific induction of the Xa27 gene by the avrXa27 transgenes in the $F_1$ plants.
Figure 4:
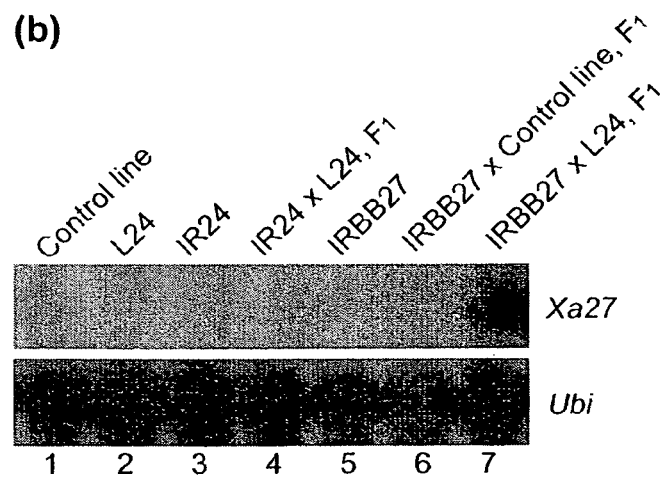

Previously we found that Xa27 in IRBB27(Xa27/Xa27) was specifically induced by type-III effector avrXa27 from incompatible *X. oryzae* pv. *oryzae* strains (Gu et al., 2005). To investigate whether the avrXa27 gene in rice has similar function, we crossed IRBB27 with the transgenic avrXa27 lines and the control plants, respectively. Messenger RNA (mRNA) isolated from the $F_1$ plants derived from those crosses were subjected to northern blot analysis for Xa27 induction. Xa27 was constitutively induced in the $F_1$ plants derived from the cross between IRBB27 and the transgenic avrXa27 lines (FIG. 4a, lanes 2-5). Compared with high Xa27 expression in the $F_1$ plants of IRBB27×L24, the Xa27 expression in the $F_1$ plants derived from the crosses between IRBB27 and L1, L14 or L25 were lower (FIG. 4a, lanes 2-5). No signal was detected in the $F_1$ plants derived from the cross between IRBB27 and the control transgenic plants (FIG. 4a, lane 1).

IR24 (xa27/xa27) carries susceptible alleles of the Xa27 gene, which shares identical coding regions with Xa27 but was not induced by *X. oryzae* pv. *oryzae* strains harboring avrXa27 (Gu et al., 2005). This resistance specificity was retained between Xa27 (or xa27) and the avrXa27 gene in rice. The susceptible allele xa27 in IR24 was not induced in the $F_1$ plants derived from the cross between IR24 and L24 (FIG. 4b, lane 4). Our results indicate that the avrXa27 gene in rice was as functional as that in bacteria in the specific induction of Xa27 expression. These results are consistent with and supplementary to our previous finding that Xa27 is specifically induced in the presence of type-III effector avrXa27. In this case, avrXa27 was generated from the expression of the avrXa27 gene in rice.

Example 7

Figure 5:
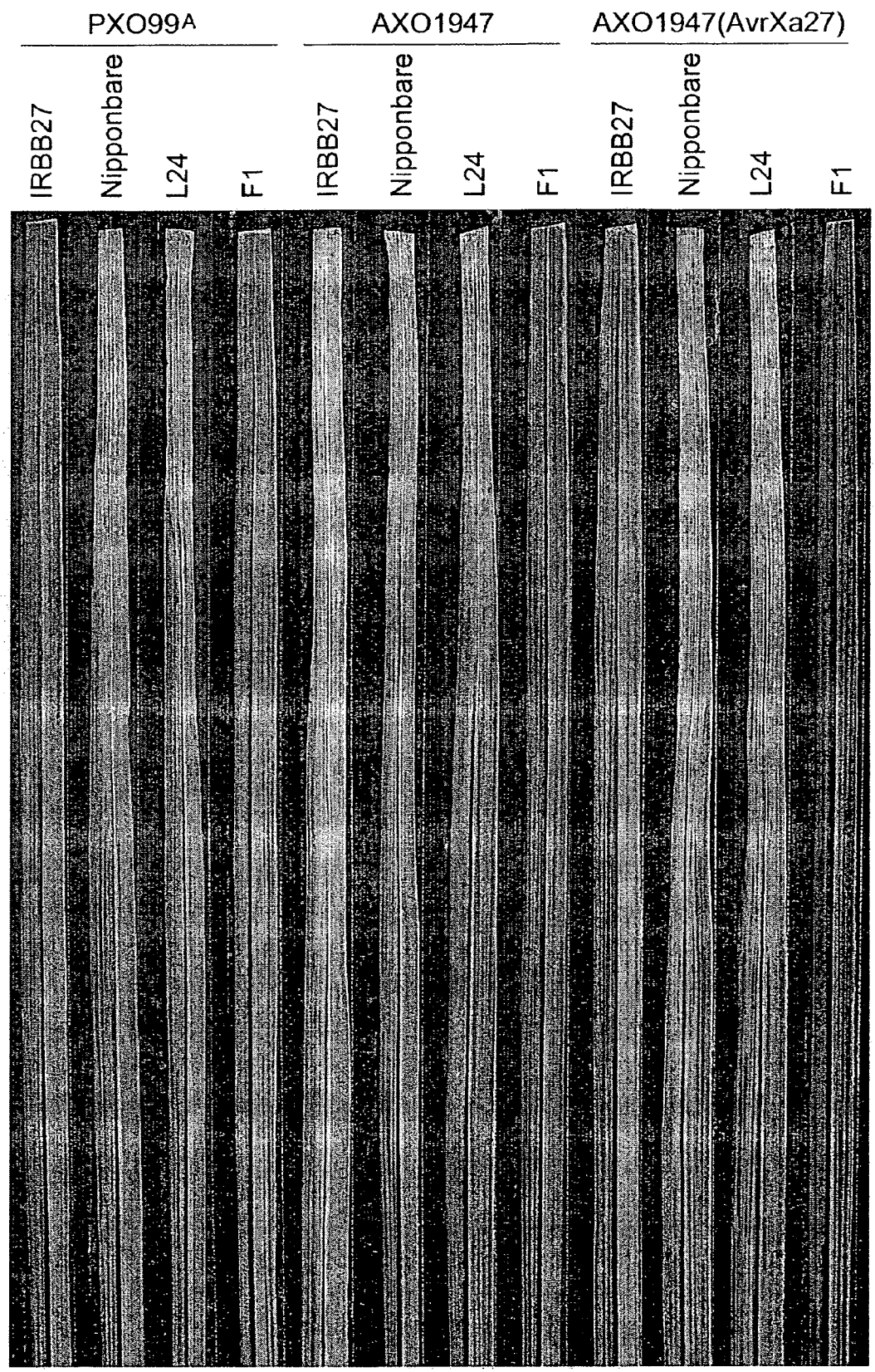
FIG. 5 shows that the $F_1$ plants of IRBB27×L24 conferred resistance to both incompatible and compatible X. oryzae pv. oryzae strains. Both PXO99$^A$ and AXO1947 (pHM1avrXa27) are incompatible X. oryzae pv. oryzae strains on IRBB27 plants that carry the wild-type Xa27 gene while AXO1947 is a compatible strain. Nipponbare is the wild-type japonica variety. L24 is the transgenic avrXa27 line in Nipponbare background. Both Nipponbare and L24 are susceptible to all bacterial strains tested. The $F_1$ plants ($F_1$) are derived from the cross between IRBB27 and L24.

Disease Evaluation of the $F_1$ Plants from Crosses Between IRBB27 and Transgenic avrXa27 Lines Our previous study showed that ectopic expression of Xa27 under the control of the rice PR1 promoter conferred resistance to both incompatible and compatible strains of *X. oryzae* pv. *oryzae* (Gu et al., 2005). To investigate whether the induction of Xa27 by the avrXa27 gene in rice function in a similar manner for resistance to bacterial blight, we carried out disease evaluation of the $F_1$ plants derived from the crosses between IRBB27 plants (F) and the transgenic avrXa27 lines (F) for resistance to bacterial blight. The $F_1$ plants of IRBB27×L24 were inoculated with either Xa27-incompatible strain (PXO99[A]) or Xa27-compatible strains (AXO1947, K202 and ZHE173). The $F_1$ plants derived from the crosses between IRBB27 and L24 not only showed complete resistance to PXO99[A] but also conferred broad-spectrum complete resistance to three otherwise compatible strains (FIG. 5 and Table 1). Enhanced resistance to compatible strain AXO1947 was also observed in the $BC_1F_1$ plants derived from the backcrosses between IRBB27 and L1, L14, L24 and L25 (Table 2). In the control experiments, IRBB27 conferred resistance to incompatible strain PXO99[A] (Table 2). The control $F_1$ plants derived from the cross between IRBB27 and the control line were partially resistant to incompatible strain PXO99[A] and susceptible to three compatible strains while the $F_1$ plants derived from the cross between IR24 and L24 were susceptible to all strains tested (Table 1).

TABLE 2

Disease Evaluation of Wild-Type Plants, Transgenic Lines and Their
$F_1$ Progeny to Various *X. oryzae* pv. *oryzae* Strains[a]

| | *X. oryzae* pv. *oryzae* strain | | | |
|---|---|---|---|---|
| Plant | PXO99[A] | AXO1947 | K202 | ZHE173 |
| Control line[b] | 19.6 ± 4.2(S) | 19.5 ± 2.8(S) | 16.4 ± 2.3(S) | 18.8 ± 3.6(S) |
| L24 | 20.2 ± 2.4(S) | 16.9 ± 2.5(S) | 16.5 ± 3.1(S) | 14.0 ± 3.2(S) |
| IR24 | 29.0 ± 3.6(S) | 27.5 ± 3.1(S) | 19.9 ± 3.5(S) | 24.5 ± 4.3(S) |
| IRBB27 | 0.3 ± 0.2(R) | 28.6 ± 5.0(S) | 23.3 ± 2.3(S) | 27.3 ± 3.5(S) |
| IR24 × L24, $F_1$ | 35.9 ± 6.6(S) | 38.1 ± 4.8(S) | 21.4 ± 2.9(S) | 25.4 ± 4.7(S) |
| IRBB27 × Control line, $F_1$ | 5.3 ± 6.3(MR) | 20.7 ± 3.2(S) | 20.4 ± 4.7(S) | 18.9 ± 9.6(S) |
| IRBB27 × L24, $F_1$ | 0.4 ± 0.4(R) | 0.3 ± 0.2(R) | 0.1 ± 0.1(R) | 0.2 ± 0.2(R) |
| IRBB27 × L1, $BC_1F_1$ | ND | 0.6 ± 0.6(R) | ND | ND |

TABLE 2-continued

Disease Evaluation of Wild-Type Plants, Transgenic Lines and Their
$F_1$ Progeny to Various *X. oryzae* pv. *oryzae* Strains[a]

| | X. oryzae pv. oryzae strain | | | |
|---|---|---|---|---|
| Plant | PXO99[A] | AXO1947 | K202 | ZHE173 |
| IRBB27 × L14, $BC_1F_1$ | ND | 1.2 ± 0.4(R) | ND | ND |
| IRBB27 × L25, $BC_1F_1$ | ND | 0.6 ± 0.9(R) | ND | ND |

[a]The average lesion length and standard deviation are calculated based on two independent experiments. For each strain, at least 60 leaves from eight individual plants were inoculated. For resistance score, refer to Materials and Methods. R, resistant; S, susceptible; MR, moderately resistant; MS, moderately susceptible; ND, not detected.
[b]Control line was produced by transformation of Nipponbare with empty vector pC1305.1. For crosses, either L24 or the control transgenic plant was used as pollen donor.

Example 8

The Xa27 Expression Induced by the avrXa27 Transgene also Provided Enhanced Resistance to *X. oryzae* pv. *oryzicola*

Figure 6:
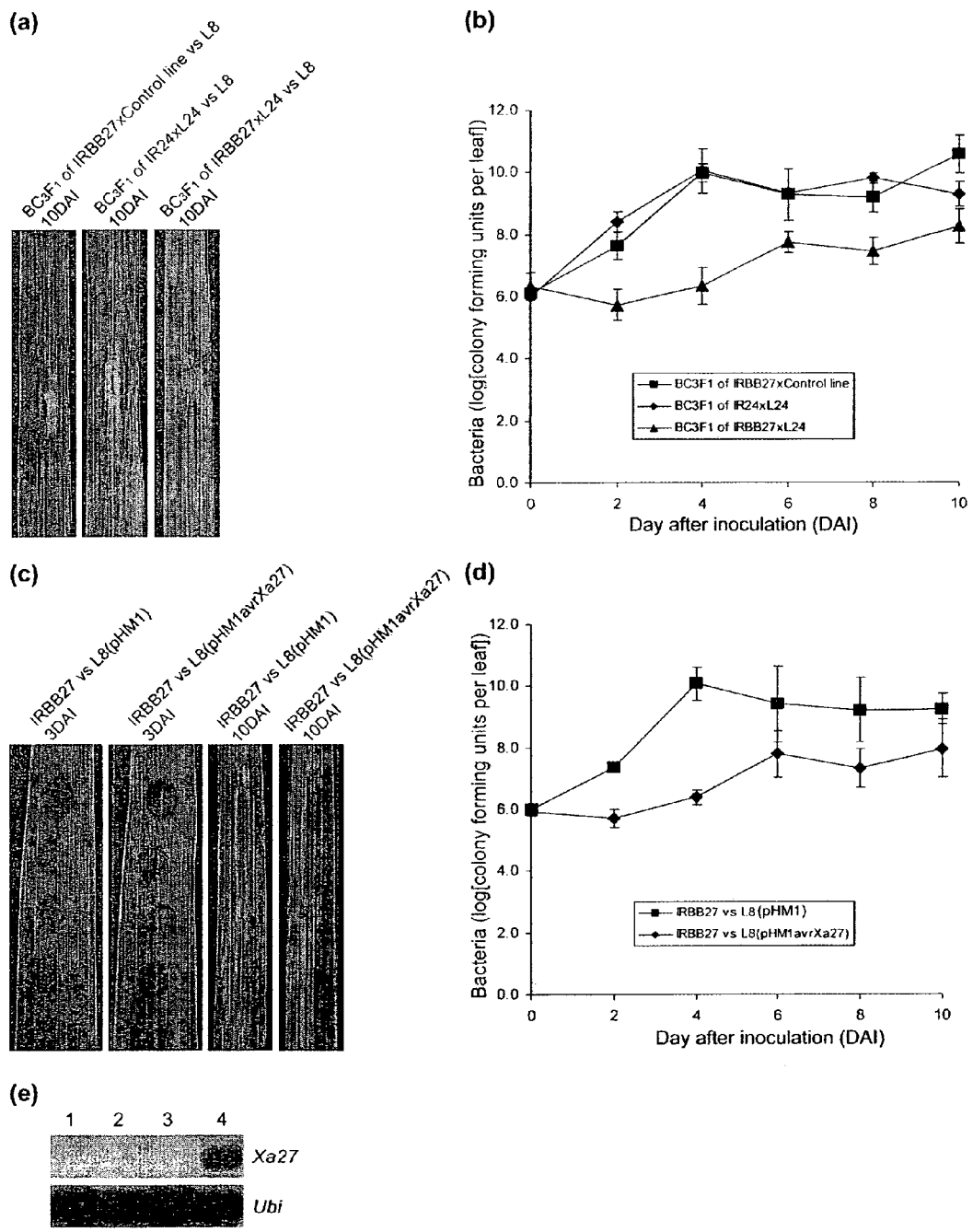
FIGS. 6a-6e show the expression of the Xa27 gene confers enhanced resistance to X. oryzae pv. oryzicola.

In the $BC_3F_1$ plants of IRBB27×Control line or IR24×L24, no Xa27 expression was detected due to absence of Xa27 or avrXa27 genes (data not shown). At 10 days after inoculation with *X. oryzae* pv. *oryzicola* strain L8, large disease lesions of bacterial leaf streak were developed in both directions towards leaf base and leaf tip on leaves of these $BC_3F_1$ plants (FIG. 6*a*, leaves 1 and 2). A lot of yellow beads of *X. oryzae* pv. *oryzicola* were observed on the leaf surface (FIG. 6*a*, leaves 1 and 2). In $BC_3F_1$ plants of IRBB27×L24, the Xa27 gene was induced by the avrXa27 gene from L24 (data not shown). The $BC_3F_1$ plants of IRBB27×L24 had smaller lesions of bacterial leaf streak than those on the $BC_3F_1$ plants of IRBB27×Control line or IR24×L24 (FIG. 6*a*, leaf 3). However, yellow beads of *X. oryzae* pv. *oryzicola* were still observed at the margins of lesions on the $BC_3F_1$ plants of IRBB27×L24 (FIG. 6*a*, leaf 3). The later result indicates that Xa27-mediated enhanced resistance to *X. oryzae* pv. *oryzicola* strain L8 is partial or incomplete. This was further verified by the fact that bacterial populations in the inoculated leaves of the $BC_3F_1$ plants of IRBB27×L24 still kept growing over 10 days after syringe infiltration (FIG. 6*b*). However, the bacterial populations in the inoculated leaves of the $BC_3F_1$ plants of IRBB27×L24 were 10- to 5000-fold lower than those in the control $BC_3F_1$ plants (FIG. 6*b*).

To further verify that the enhanced resistance to *X. oryzae* pv. *oryzicola* strain L8 was resulted from Xa27 expression, we inoculated IRBB27 plants with *X. oryzae* pv. *oryzicola* strain L8 with or without the avrXa27 gene. At 3 days after syringe infiltration of bacterium, leaf tissues at infection sites in both interactions turned brown (FIG. 6*c*, leaves 1 and 2). However, few or no tiny yellow beads of bacteria was found on the IRBB27 plants inoculated with *X. oryzae* pv. *oryzicola* L8(pHM1avrXa27) while a lot of bacterial beads were observed at the infection sites on the leaves of IRBB27 plants inoculated with *X. oryzae* pv. *oryzicola* L8(pHM1) (FIG. 6*c*, leaves 1 and 2). At 10 days after infection, the disease lesions of bacterial leaf streak on the IRBB27 plants inoculated with L8(pHM1avrXa27) were smaller and more restricted than those on the IRBB27 plants inoculated with L8(pHM1) (FIG. 6*c*, leaves 3 and 4). Similarly, the bacterial populations in the leaves of IRBB27 plants infiltrated with L8(pHM1avrXa27) were 8- to 8373-fold lower than those in the IRBB27 plants inoculated with L8(pHM1) (FIG. 6*d*). In addition, induction of Xa27 in IRBB27 by avrXa27 from L8(pHM1avrXa27) was detected at 3 days after inoculation while no induction was found when L8(pHM1) was used for inoculation (FIG. 6*e*).

In conclusion, Xa27 ectopic lines conferred resistance to incompatible and compatible *X. oryzae* pv. *oryzae* strains (Gu et al., 2005). Here, we have generated another type of Xa27 ectopic lines with broad-spectrum resistance to *X. oryzae* pv. *oryzae* strains and enhanced resistance to *X. oryzae* pv. *oryzicola* by induction of the wild-type allele of the Xa27 gene with the avrXa27 transgene in rice.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Alfano, J. R., and Collmer, A. (2004). Type III secretion system effector proteins: double agent in bacterial disease and plant defense. Annu. Rev. Phytopathol. 42:385-414.
Allison, R. F. et al. (1985). Sequence determination of the capsid protein gene and flanking regions of tobacco etch virus: Evidence for synthesis and processing of a polyprotein in potyvirus genome expression. Proc. Natl. Acad. Sci. USA 82:3969-3972.

Amante-Bordeos, A. et al. (1992). Transfer of bacteria blight and blast !resistance from the tetraploid wild rice *Oryza minuta* to cultivated rice, *Oryza sativa*. Theor Appl Genet 84:345-354.

Atanassova, R. et al. (1992). A 126 by fragment of a plant histone gene promoter confers preferential expression in meristems of transgenic *Arabidopsis*. Plant J. 2:291-300

Bai, J. et al. (2000). *Xanthomonas oryzae* pv. *oryzae* avirulence genes contribute differently and specifically to pathogen aggressiveness. Mol. Plant-Mircobe Interact. 13:1322-1329.

Binding (1985). "Regeneration of Plants," In Plant Protoplasts, Fowke, L. C. and Constabel, F. (eds), pp. 21 73, CRC Press, Boca Raton.

Bonas, U. et al. (1989). Genetic and structural characterization of the avirulence gene avrBs3 from *Xanthomonas campestris* pv. *vesicatoria*. Mol. Gen. Genet. 218:127-136.

Callis, J. et al. (1987). Introns increase gene expression in cultured maize cells. Genes Dev. 1:1183-1200.

Chen, H. et al. (2002). A new gene for bacterial blight resistance in rice located on chromosome 12 identified from Minghui 63, an elite restorer line. Phytopathology 92:750-754.

Chen, W. et al. (1996). The promoter of a H2O2-inducible, *Arabidopsis* glutathione S-transferase gene contains closely linked OBF- and OBP1-binding sites. Plant J. 10: 955-966.

Chen, Z. et al. (2000). The *Pseudomonas syringae* avrRpt2 gene product promotes pathogen virulence from inside plant cells. Mol. Plant-Microbe Interact. 13:1312-1321.

Chen, Z. et al. (2004). The *Pseudomonas syringae* type III effector AvrRpt2 functions downstream or independently of SA to promote virulence on *Arabidopsis thaliana*. Plant J. 37:494-504.

Chu, Z. et al. (2006). Promoter mutations of an essential gene for pollen development result in disease resistance in rice. Genes Dev. 20: 1250-1255.

Cunnac, S. et al. (2004). Inventory and functional analysis of the large Hrp regulon in Ralstonia solanacearum: Identification of novel effector proteins translocated to plants host cells through the type III secretion system. Mol. Microbiol. 53:115-128.

De Feyter, R., and Gabriel, D. W. (1991). At least six avirulence genes are clustered on a 90-kilobase plasmid in *Xanthomonas campestris* pv. *malvacearum*. Mol. Plant-Microbe Interact. 4:423-432.

De Feyter, R. et al. (1998). Five avirulence genes from *Xanthomonas campestris* pv. *malvacearum* cause genotype-specific cell death when expressed transiently in cotton. Mol. Plant-Microbe Interact. 11, 698-701.

Deikman, J. and Fischer, R. L. (1988). Interaction of a DNA binding factor with the 5'-flanking region of an ethylene-responsive fruit ripening gene from tomato. EMBO J. 7:3315-3320.

Della-Cioppa, G. et al. (1987). Protein trafficking in plant cells. Plant Physiol. 84:965-968.

Dellaporta, S. et al. (1984). Maize DNA mini prep. In: Russell M (Ed) Molecular biology of plants: a laboratory course manual. Cold Spring Harbor Laboratory Press, Cold Spring Harbor, N.Y., pp 36-37.

Duan, Y. P. et al. (1999). Expression of a single, host-specific, bacterial pathogenicity gene in plant cells elicits division, enlargement, and cell death. Mol. Plant-Microbe Interact. 12:556-560.

Elroy-Stein, O. et al. (1989). Cap-independent translation of mRNA conferred by encephalomyocarditis virus 5' sequence improves the performance of the vaccinia virus/bacteriophage T7 hybrid expression system. Proc. Natl. Acad. Sci. USA 86:6126-6130.

Evans et al. (1983). "Protoplasts Isolation and Culture," In Handbook of Plant Cell Culture, pp. 124-176, MacMillilan Publishing Company, New York.

Flor, H. H. (1971). Current status of the gene-for-gene concept. Annu Rev Phytopathol. 9:275-96.

Fraley, R. T. et al. (1983). Expression of bacterial genes in plant cells. Proc. Natl. Acad. Sci. USA 80:4803-4807.

Fromm, M. et al. (1985). Expression of genes transferred into monocot and dicot plant cells by electroporation. Proc. Natl. Acad. Sci. USA 82:5824-5828.

Gallie, D. R. et al. (1989). In Molecular Biology of RNA, ed. Cech, Liss, New York, pp. 237-256.

Gao, D. Y. et al. (2001). Identification of a new gene for resistance to bacterial blight in a somaclonal mutant HX-3 (indica). Rice Genet Newsl. 18:66-68.

Gopalan, S. et al. (1996). Expression of the *Pseudomonas syringae* avirulence protein AvrB in plant cells alleviates its dependence on the hypersensitive response and pathogenicity (Hrp) secretion system in eliciting phenotype-specific hypersensitive cell death. Plant Cell. 8:1095-1105.

Gu, K. et al. (2004). High-resolution genetic mapping of Xa27(t), a new bacterial blight resistance gene in rice, *Oryza sativa* L. Theoretical and Applied Genetics 108:800-807.

Gu, K. et al. (2005. R gene expression induced by a type-III effector triggers disease resistance in rice. Nature 435: 1122-1125.

Gnanamanickam, S. et al. (1999). An overview of bacterial blight disease of rice and strategies for its management. Curr Sci 77:1435-1443.

Guerineau, F. et al. (1991). Effect of deletions in the cauliflower mosaic virus polyadenylation sequence on the choice of the polyadenylation sites in tobacco protoplasts. Mol. Gen. Genet. 226:141-144.

Hauck, P. et al. (2003). A *pseudomonas syringae* type III effector suppresses cell wall-based extracellular defense in susceptible *Arabidopsis* plants. Proc. Natl. Acad. Sci. USA. 100:8577-8582.

Horsch, R. B. et al. (1984). Inheritance of functional genes in plants. Science 233:496-498.

He, Q., Li, D., Znu, Y., Tan, M., Zhang, D., and Lin, X. (2006). Fine mapping of Xa2, a bacterial blight resistance gene in rce. Molecular Breeding 17:1-6.

Hopkins, C. M. et al. (1992). Identification of a family of avirulence genes from *Xanthomonas oryzae* pv. *oryzae*. Mol. Plant-Microbe Interact. 5:451-459.

Iyer, A. S., and McCouch, S. R. (2004). The rice bacterial blight resistance gene xa5 encodes a novel form of disease resistance. Mol. Plant-Microbe Interact. 17:1348-1354.

Jobling, S. A. and Gehrke, L. et al. (1987). Enhanced translation of chimaeric messenger RNAs containing a plant viral untranslated leader sequence. Nature 325:622-625.

Joshi, C. P. (1987). Putative polyadenylation signals in nuclear genes of higher plants: a compilation and analysis. Nucleic Acids Res. 15:9627-9639.

Kauffman, H. E. et al. (1973). An improved technique for evaluating resistance to rice varieties of *Xanthomonas oryzae*. Plant Dis. Rep. 57:537-541.

Khush, G. S., and Angeles, E. R. (1999). A new gene for resistance to race 6 of bacterial blight in rice, *Oryza saliva* L. Rice Genet. Newsl. 16:92-93.

Kinoshita, T. (1995). Report of Committee on gene symbolization, nomenclature and linkage groups. Rice Genet. Newsl. 12:9-115.

Kjemtrup, S. et al. (2000). Effector proteins of phytopathogenic bacteria: bifunctional signals in virulence and host recognition. Current Opinion in Microbiology 3:73-78.

Klee, H. et al. (1987). *Agrobacterium*-mediated plant transformation and its further applications to plant biology. Ann. Rev. of Plant Phys. Plant Mol. Biol. 38:467-486.

Klein, T. M. et al. (1987). High-velocity microprojectiles for delivering nucleic acids into living cells. Nature 327:70-73.

Last, D. I. et al. (1991). pEmu: an improved promoter for gene expression in cereal cells. Theor. Appl. Genet. 81:581.

Lazo, G. R. et al. (1991). A DNA transformation competent *Arabidopsis* genome library in *Arobacterium*. BioTechnology 9:963-967.

Lahaye, T., and Bonas, U. 2001. Molecular secrets of bacterial type III effector proteins. Trends Plant Sci 6:479-485

Lee, B. M. et al (2005). The genome sequence of *Xanthomonas oryzae* pathovar *oryzae* KACC10331, the bacterial blight pathogen of rice. Nucleic Acids Res 33:577-586.

Li, P. et al. (2004). avrXa3: A novel member of avrBs3 gene family from *Xanthomonas oryzae* pv. *oryzae* has a dual function. Prog Natl Sci USA 14:774-780.

Lin, X. H. et al. (1996). Identification and mapping of a new gene for bacterial blight resistance in rice based on RFLP markers. Phytopathology 86:1156-1159.

Liu, G.-Z. et al. (2002). Biochemical characterization of the kinase domain of the rice disease resistance receptor-like kinase XA21. J Biol Chem 277:20264-20269.

Liu, Z. B. (1997). A G-Box-Binding Protein from Soybean Binds to the E1 Auxin-Response Element in the Soybean GH3 Promoter and Contains a Proline-Rich Repression Domain. Plant Physiol 115:397-407.

Lommel, S. A. et al. (1991). Identification of the maize chlorotic mottle virus capsid protein cistron and characterization of its subgenomic messenger RNA. Virology 81:382-385.

Macejak, D. G. and Sarnow, P. (1991). Internal initiation of translation mediated by the 5' leader of a cellular mRNA. Nature 353:90-94.

Makino, S. et al. (2006). Inhibition of resistance Gene-mediated defense in rice by *Xanthomonas oryzae* pv. *oryzicola*. Mol Plant-Microbe Interact 19:240-249.

Marois, R. et al. (2002). The *Xanthomonas* type III effector protein AvrBs3 modulates plant gene expression and induces cell hypertrophy in the susceptible host. Mol Plant-Microbe Interact 15:637-646.

McElroy, D. et al. (1990). Isolation of an efficient actin promoter for use in rice transformation. Plant Cell 2:163-171.

McElroy, D. et al. (1991). Construction of expression vectors based on the rice actin 1 (Act1) 5' region for use in monocot transformation. Mol Gen Genet 231:150-160.

McNellis, T. W. et al. (1998). Glucocorticoid-inducible expression of a bacterial avirulence gene in transgenic *Arabidopsis* induces hypersensitive cell death. Plant J. 14:247-258.

Mew, T. W. (1987). Current status and future prospects of research on bacterial blight of rice. Annual Review of Phytopathology 25:359-382

Mogen, B. D. et al. (1990). Upstream sequences other than AAUAAA are required for efficient messenger RNA 3'-end formation in plants. Plant Cell 2:1261-1272.

Munroe, D. and Jacobson, A. (1990). Tales of poly(A): a review. Gene 91:151-158.

Murray, E. E. et al. (1989). Codon usage in plant genes. Nucleic Acids Res. 17:477-498.

Nino-Liu, D. et al. (2006). *Xanthomonas oryzae* pathovars: model pathogens of a model crop. Molecular Plant Pathology 7:303-324.

Ogawa, T. (1993). Methods and strategy for monitoring race distribution and identification of resistance genes to bacterial leaf blight (Xanthomonas oryzae pv oryzae) in rice. JARQ 27:71-80.

Ou, S. H. (1985). Rice Diseases. Kew, Surrey: Commonwealth Agricultural Bureau.

Paszkowski, J. et al. (1984). Direct gene transfer to plants. EMBO J. 3:2717-2722.

Proudfoot, N. (1991). Poly(A) signals. Cell 64:671-674.

Redolfi, P. et al. (1983). Occurrence of pathogenesis-related (b) and similar proteins in different plant species. Neth. J. Plant Pathol. 89:245-254.

Rocha-Sosa, M. et al. (1989). Both developmental and metabolic signals activate the promoter of a class I patatin gene. EMBO J., 8:23-29.

Ronald, P. C. (1997). The molecular basis of disease resistance in rice. Plant Mol. Biol. 35:179-186.

Sakai, T. et al. (1996). Analysis of the promoter of the auxin-inducible gene, parC, of tobacco. Plant Cell Physiol. 37:906-913.

Samac, D. A. et al. (1990). Isolation and Characterization of the Genes Encoding Basic and Acidic Chitinase in *Arabidopsis thaliana*. Plant Physiol., 93:907-914.

Sambrook, J. et al. (1989). Molecular Cloning a laboratory manual (2nd ed.). Cold Spring Harbor Laboratory Press, Cold Spring Harbor Laboratory, N.Y.

Sanfacon, H. et al. (1991). A dissection of the cauliflower mosaic virus polyadenylation signal. Genes Dev. 5:141-149.

Schaad, N. W. et al. (1996). An improved infiltration technique to test the pathogenicity of *Xanthomonas oryzae* pv. *oryzae* in rice seedlings. Seed Sci Technol 24:449-456.

Schornack, S. et al. (2006). Gene-for-gene-mediated recognition of nuclear-targeted AvrBs3-like bacterial effector proteins. J. Plant Physiol. 163:256-272.

Scofield, S. R. et al. (1996). Molecular basis of gene-for-gene specificity in bacterial speck disease of tomato. Science 274:2063-2065.

Sheen, J. (1996). Ca2+-dependent protein kinases and stress signal transduction in plants. Science 274:1900-1902.

Sheng, Z.-J. et al. (2005). Detection of QTL conferring resistance to bacterial leaf streak in rice chromosome 2 (*O. sativa* L. spp. indica). Scientia Agric Sinica 38:1923-1925.

Song, W. Y. et al. (1995). A receptor kinase-like protein encoded by the rice disease resistance gene, Xa21. Science 270:1804-1806.

Stevens, C. et al. (1998). Sequence variation in allele of avirulence gene avrPphE.R2 from *Pseudomonas syringe* pv. *phaseolicola* lead to loss of recognition of the AvrPphE protein within bean cells and a gain in cultivar-specific virulence. Mol. Microbiol. 29:165-177.

Streit, W. R. and Phillips, D. A. (1997). A biotin-regulated locus, bioS, in a possible survival operon of *Rhizobium meliloti*. Mol. Plant. Microbe Interact. 10:933-937.

Sun, X. et al. (2004). Xa26, a gene conferring resistance to *Xanthomonas oryzae* pv. *oryzae* in rice, encodes an LRR receptor kinase-like protein. Plant J. 37:517-527.

Tang, D. et al. (2000). Mapping of QTLs conferring resistance to bacterial leaf streak in rice. Theor Appl Genet 101:286-291.

Tang, X. et al. (1996). Initiation of plant disease resistance by physical interaction of AvrPto and Pto kinase. Science 274, 2060-2063

Tierney, M. L. et al. (1987). Isolation and characterization of a genomic clone encoding the β-subunit of β-conglycinin. Planta 172:356-363.

Tomes et al. (1995). "Direct DNA Transfer into Intact Plant Cells via Microprojectile Bombardment," In Plant Cell, Tissue, and Organ Culture: Fundamental Methods, ed. Gamborg and Phillips, Springer-Verlag, Berlin.

Uknes, S. et al. (1992). Acquired resistance in *Arabidopsis*. Plant Cell 4:645-656 (1992)

Van den Ackerveken, G. et al. (1996). Recognition of the bacterial avirulence protein AvrBs3 occurs inside the host plant cell. Cell 87:1307-1316.

Van Loon, L. C. (1985). Pathogenesis-related proteins. Plant Mol. Biol. 4:111-116.

Vasil, I. R. (ed.) (1984). Cell Culture and Somatic Cell Genetics of Plants, Vol. I, Academic Press, Orlando.

Vasil, I. R. (ed.) (1986). Cell Culture and Somatic Cell Genetics of Plants, Vol. III, Academic Press, Orlando.

Vera Cruz, C. M. et al. (2000). Predicting durability of a disease resistance gene based on an assessment of the fitness loss and epidemiological consequences of avirulence gene mutation. Proc. Natl. Acad. Sci. USA 97:13500-13505.

Weising, K. et al. (1988). Foreign genes in plants: transfer, structure, expression, and applications. Ann. Rev. Genet. 22:421-477.

Xu, Y. et al. (1995). Characterization of a rice gene family encoding root-specific proteins. Plant Mol. Biol. 27:237-248.

Yang, B. et al. (2000). The virulence factor AvrXa7 of *Xanthomonas oryzae* pv. *oryzae* is a type III secretion pathway-dependent nuclear-localized double-stranded DNA-binding protein. Proc. Natl. Acad. Sci. USA 97:9807-9812.

Yang, Y. et al. (1996). Watersoaking function(s) of XcmH1005 are redundantly encoded by members of the *Xanthomonas* avr/pth gene family. Mol. Plant-Mocrobe Interact. 9:105-113.

Yang, Z. et al. (2003). Genetic and physical mapping of a new gene for bacterial blight resistance in rice. Theor. Appl. Genet. 106:1467-1472.

Yin, Z. and Wang, G. L. (2000). Evidence of multiple complex patterns of T-DNA integration into the rice genome. Theor. Appl. Genet. 100:461-470.

Yoshimura, S. et al. (1998). Expression of Xa1, a bacterial blight-resistance gene in rice, is induced by bacterial inoculation. Proc. Natl. Acad. Sci. USA 95:1663-1668

Young, S. A. et al. (1996). Changes in the plasma membrane distribution of phospholipase D during resistant interactions with *Xanthomonas oryzae* pv. *oryzae*. Plant Cell. 8:1079-1090.

Zhang, Q. et al. (1998). Identification and tagging a new gene for resistance to bacterial blight (*Xanthomonas oryzae* pv *oryzae*) from *O. rufipogon*. Rice Genet. Newsl. 15:138-142.

Zhu, W. G. et al. (1998). AvrXa10 contains an acidic transcriptional activation domain in the functionally conserved C terminus. Mol. Plant-Microbe Interact. 11:824-832.

---

What is claimed is:

1. A transgenic plant containing within its genome a first nucleic acid operably linked to a promoter that is active in the plant, wherein the first nucleic acid encodes an avrXa27 protein having the amino acid sequence set forth in SEQ ID NO:2.

2. The transgenic plant of claim 1, wherein the first nucleic acid has the nucleotide sequence set forth in SEQ ID NO:1.

3. The transgenic plant of claim 1, wherein the first promoter is selected from the group consisting of a constitutive promoter, an inducible promoter or a tissue specific promoter.

4. The transgenic plant of claim 1, wherein the plant further contains within its genome a second nucleic acid operably linked to a second promoter that is active in a plant, wherein the second nucleic acid encodes an Xa27 protein having an amino acid sequence set forth in SEQ ID NO:4.

5. The transgenic plant of claim 4, wherein the second nucleic acid has the nucleotide sequence set forth in SEQ ID NO:3.

6. The transgenic plant of claim 4, wherein the plant is non-transgenic for the nucleic acid encoding the Xa27 protein.

7. The transgenic plant of claim 4, wherein the plant is transgenic for the nucleic acid encoding the Xa27 protein.

8. The transgenic plant of claim 7, wherein the second promoter is native Xa27 promoter.

9. The transgenic plant of claim 1, wherein the plant is rice.

10. The transgenic plant of claim 1, wherein the plant is selected from the group consisting of pepper, tomato, beans, cotton, cucumber, cabbage, barley, oats, wheat, corn and citrus.

11. A plant containing within its genome a first nucleic acid operably linked to a first promoter that is active in the plant and a second nucleic acid operably linked to a second promoter that is active in the plant, wherein the first nucleic acid encodes an avrXa27 protein having the amino acid sequence set forth in SEQ ID NO:2 and wherein the second nucleic acid encodes an Xa27 protein having an amino acid sequence set forth in SEQ ID NO:4.

12. The plant of claim 11, wherein the first nucleic acid has the nucleotide sequence set forth in SEQ ID NO:1.

13. The plant of claim 11, wherein the second nucleic acid has the nucleotide sequence set forth in SEQ ID NO:3.

14. The plant of claim 11, wherein the first promoter is selected from the group consisting of a constitutive promoter, an inducible promoter or a tissue specific promoter and the second promoter is a native Xa27 promoter.

15. The plant of claim 11, wherein the plant is obtained by crossing a first plant containing a native nucleic acid encoding the Xa27 protein with a transgenic plant containing the first nucleic acid.

16. The plant of claim 11, wherein the plant is obtained by crossing a first transgenic plant containing the second nucleic acid with a second transgenic plant containing the first nucleic acid.

17. The plant of claim 11, wherein the plant is rice.

18. The plant of claim 11, wherein the plant is selected from the group consisting of pepper, tomato, beans, cotton, cucumber, cabbage, barley, oats, wheat, corn and citrus.

19. A method of inducing expression of Xa27 gene in a plant which comprises expressing a nucleic acid in the plant, wherein the nucleic acid is operably linked to a promoter that is active in the plant and wherein the nucleic acid encodes an avrXa27 protein having the amino acid sequence set forth in SEQ ID NO:2.

20. The method of claim 19, wherein the nucleic acid has the nucleotide sequence set forth in SEQ ID NO:1.

21. The method of claim 19, wherein the promoter is selected from the group consisting of a constitutive promoter, an inducible promoter or a tissue specific promoter.

22. The method of claim 19, wherein the plant is rice.

23. The method of claim 21, wherein the plant is selected from the group consisting of pepper, tomato, beans, cotton, cucumber, cabbage, barley, oats, wheat, corn and citrus.

24. A method of generating an enhanced and broad spectrum resistance to bacterial blight in a plant which comprises inducing the expression of Xa27 gene in a plant by expressing a nucleic acid in the plant, wherein the nucleic acid is operably linked to a promoter that is active in the plant and wherein the nucleic acid encodes an avrXa27 protein having the amino acid sequence set forth in SEQ ID NO:2.

25. The method of claim 24, wherein the nucleic acid has the nucleotide sequence set forth in SEQ ID NO:1.

26. The method of claim 24, wherein the promoter is selected from the group consisting of a constitutive promoter, an inducible promoter or a tissue specific promoter.

27. The method of claim 24, wherein the plant is rice.

28. The method of claim 24, wherein the plant is selected from the group consisting of pepper, tomato, beans, cotton, cucumber, cabbage, barley, oats, wheat, corn and citrus.

29. The method of claim 24, wherein expression of the Xa27 gene is induced in a plant infected with bacterial blight.

30. A method of generating an enhanced resistance to bacterial leaf streak in a plant which comprises inducing the expression of Xa27 gene in a plant by expressing a nucleic acid in the plant, wherein the nucleic acid is operably linked to a promoter that is active in the plant and wherein the nucleic acid encodes an avrXa27 protein having the amino acid sequence set forth in SEQ ID NO:2.

31. The method of claim 30, wherein the nucleic acid has the nucleotide sequence set forth in SEQ ID NO:1.

32. The method of claim 30, wherein the promoter is selected from the group consisting of a constitutive promoter, an inducible promoter or a tissue specific promoter.

33. The method of claim 30, wherein the plant is rice.

34. The method of claim 30, wherein the plant is selected from the group consisting of pepper, tomato, beans, cotton, cucumber, cabbage, barley, oats, wheat, corn and citrus.

35. The method of claim 30, wherein the expression of the Xa27 gene is induced in a plant infected with bacterial leaf streak.

* * * * *